US012797602B2

(12) United States Patent
Tuval et al.

(10) Patent No.: US 12,797,602 B2
(45) **Date of Patent: *Nov. 17, 2026**

(54) VENTRICULAR ASSIST DEVICE

(71) Applicant: Magenta Medical Ltd., Kadima (IL)

(72) Inventors: Yosi Tuval, Even Yehuda (IL); Daniel Glozman, Kfar Yona (IL); Gad Lubinsky, Ein Vered (IL)

(73) Assignee: Magenta Medical Ltd., Kadima (IL)

( * ) Notice: Subject to any disclaimer, the term of this patent is extended or adjusted under 35 U.S.C. 154(b) by 249 days.

This patent is subject to a terminal disclaimer.

(21) Appl. No.: 18/764,668

(22) Filed: Jul. 5, 2024

(65) Prior Publication Data

US 2024/0358998 A1 Oct. 31, 2024

Related U.S. Application Data

(63) Continuation of application No. 17/574,701, filed on Jan. 13, 2022, now Pat. No. 12,090,314, which is a (Continued)

(51) Int. Cl.
*A61M 60/414* (2021.01)
*A61M 60/139* (2021.01)

(Continued)

(52) U.S. Cl.
CPC ........ *A61M 60/414* (2021.01); *A61M 60/139* (2021.01); *A61M 60/148* (2021.01);

(Continued)

(58) Field of Classification Search
CPC .... A61M 1/122; A61M 1/1086; A61M 1/125; A61M 2205/3334; A61M 1/1031;

(Continued)

(56) References Cited

U.S. PATENT DOCUMENTS 3,592,183 A 7/1971 Watkins et al.
3,932,068 A 1/1976 Zimmermann (Continued)

FOREIGN PATENT DOCUMENTS

AU 2008219653 A1 9/2008
AU 2013205145 A1 5/2013

(Continued)

OTHER PUBLICATIONS

Corrected Notice of Allowance for U.S. Appl. No. 16/275,559 mailed Nov. 8, 2023.

(Continued)

*Primary Examiner* — Deborah L Malamud
(74) *Attorney, Agent, or Firm* — Ballard Spahr LLP

(57) ABSTRACT

Apparatus and methods are described including a tube configured to traverse an aortic valve of a subject. A frame is disposed within at least a portion of the tube. An impeller rotates such as to pump blood from the subject's left ventricle to the subject's aorta. The impeller is disposed inside the tube such that, when the impeller and the tube are deployed inside the subject, and prior to rotation of the impeller, a radial gap between an outer edge of the impeller and an inner surface of the tube is less than 1 mm. The impeller is radially stabilized such that, during rotation of the impeller, a radial gap between the outer edge of the impeller and the inner surface of the tube is maintained. Other applications are also described.

21 Claims, 10 Drawing Sheets

Related U.S. Application Data continuation of application No. 16/277,411, filed on Feb. 15, 2019, now Pat. No. 11,260,212, which is a continuation of application No. PCT/IL2017/051158, filed on Oct. 23, 2017.

(60) Provisional application No. 62/543,540, filed on Aug. 10, 2017, provisional application No. 62/412,631, filed on Oct. 25, 2016.

(51) Int. Cl.
*A61M 60/148* (2021.01)
*A61M 60/17* (2021.01)
*A61M 60/237* (2021.01)
*A61M 60/806* (2021.01)
*A61M 60/825* (2021.01)

(52) U.S. Cl.
CPC .......... *A61M 60/17* (2021.01); *A61M 60/237* (2021.01); *A61M 60/806* (2021.01); *A61M 60/825* (2021.01); *A61M 2205/3334* (2013.01); *A61M 2230/30* (2013.01)

(58) Field of Classification Search
CPC .. A61M 2205/3327; A61M 2205/3365; A61M 25/00; A61M 2205/04; A61M 5/14276; A61N 1/05
See application file for complete search history.

(56) References Cited

U.S. PATENT DOCUMENTS

| | | | |
|---|---|---|---|
| 4,407,271 | A | 10/1983 | Schiff |
| 4,625,712 | A | 12/1986 | Wampler |
| 4,753,221 | A | 6/1988 | Kensey et al. |
| 4,771,765 | A | 9/1988 | Choy et al. |
| 4,909,787 | A | 3/1990 | Danforth |
| 4,919,647 | A | 4/1990 | Nash |
| 4,944,722 | A | 7/1990 | Carriker et al. |
| 4,954,055 | A | 9/1990 | Raible et al. |
| 4,957,504 | A | 9/1990 | Chardack |
| 4,964,864 | A | 10/1990 | Summers et al. |
| 4,969,865 | A | 11/1990 | Hwang et al. |
| 4,985,014 | A | 1/1991 | Orejola |
| 5,011,469 | A | 4/1991 | Buckberg et al. |
| 5,037,403 | A | 8/1991 | Garcia |
| 5,061,256 | A | 10/1991 | Wampler |
| 5,141,338 | A | 8/1992 | Asada et al. |
| 5,169,378 | A | 12/1992 | Figuera |
| 5,275,580 | A | 1/1994 | Yamazaki |
| 5,330,484 | A | 7/1994 | Guenther et al. |
| 5,348,545 | A | 9/1994 | Shani et al. |
| 5,453,076 | A | 9/1995 | Kiyota et al. |
| 5,507,629 | A | 4/1996 | Jarvik |
| 5,531,789 | A | 7/1996 | Yamazaki et al. |
| 5,533,987 | A | 7/1996 | Pray et al. |
| 5,569,275 | A | 10/1996 | Kotula et al. |
| 5,613,935 | A | 3/1997 | Jarvik |
| 5,692,882 | A | 12/1997 | Bozeman et al. |
| 5,713,730 | A | 2/1998 | Nose et al. |
| 5,749,855 | A | 5/1998 | Reitan |
| 5,772,693 | A | 6/1998 | Brownlee |
| 5,843,158 | A | 12/1998 | Lenker et al. |
| 5,863,179 | A | 1/1999 | Westphal et al. |
| 5,876,385 | A | 3/1999 | Ikari et al. |
| 5,879,499 | A | 3/1999 | Corvi |
| 5,911,685 | A | 6/1999 | Siess et al. |
| 5,911,715 | A | 6/1999 | Berg et al. |
| 5,928,132 | A | 7/1999 | Leschinsky |
| 5,947,892 | A | 9/1999 | Benkowski et al. |
| 5,957,672 | A | 9/1999 | Aber |
| 5,964,694 | A | 10/1999 | Siess et al. |
| 6,007,478 | A | 12/1999 | Siess et al. |
| 6,059,760 | A | 5/2000 | Sandmore et al. |
| 6,086,527 | A | 7/2000 | Talpade |
| 6,110,163 | A | 8/2000 | Voda |
| 6,116,862 | A | 9/2000 | Rau et al. |
| 6,135,729 | A | 10/2000 | Aber |
| 6,136,025 | A | 10/2000 | Barbut et al. |
| 6,162,017 | A | 12/2000 | Raible |
| 6,176,848 | B1 | 1/2001 | Rau et al. |
| 6,183,220 | B1 | 2/2001 | Ohara et al. |
| 6,217,541 | B1 | 4/2001 | Yu |
| 6,247,892 | B1 | 6/2001 | Kazatchkov et al. |
| 6,270,477 | B1 | 8/2001 | Bagaoisan et al. |
| 6,355,001 | B1 | 3/2002 | Quinn et al. |
| 6,413,222 | B1 | 7/2002 | Pantages et al. |
| 6,482,228 | B1 | 11/2002 | Norred |
| 6,485,501 | B1 | 11/2002 | Green |
| 6,506,146 | B1 | 1/2003 | Mohl |
| 6,520,983 | B1 | 2/2003 | Colgan et al. |
| 6,533,716 | B1 | 3/2003 | Schmitz-Rode et al. |
| 6,533,770 | B1 | 3/2003 | Lepulu et al. |
| 6,537,315 | B2 | 3/2003 | Yamazaki et al. |
| 6,544,216 | B1 | 4/2003 | Sammler et al. |
| 6,592,567 | B1 | 7/2003 | Levin et al. |
| 6,616,624 | B1 | 9/2003 | Kieval |
| 6,709,429 | B1 | 3/2004 | Schaefer et al. |
| 6,884,210 | B2 | 4/2005 | Nose et al. |
| 6,949,066 | B2 | 9/2005 | Bearnson et al. |
| 6,974,436 | B1 | 12/2005 | Aboul-Hosn et al. |
| 7,004,925 | B2 | 2/2006 | Navia et al. |
| 7,010,954 | B2 | 3/2006 | Siess et al. |
| 7,011,620 | B1 | 3/2006 | Siess |
| 7,022,100 | B1 | 4/2006 | Aboul-hosn et al. |
| 7,027,875 | B2 | 4/2006 | Siess et al. |
| 7,070,555 | B2 | 7/2006 | Siess |
| 7,144,364 | B2 | 12/2006 | Barbut et al. |
| 7,159,593 | B2 | 1/2007 | Mccarthy et al. |
| 7,201,772 | B2 | 4/2007 | Schwammenthal et al. |
| 7,258,679 | B2 | 8/2007 | Moore et al. |
| 7,335,192 | B2 | 2/2008 | Keren et al. |
| 7,338,521 | B2 | 3/2008 | Antaki et al. |
| 7,341,570 | B2 | 3/2008 | Keren et al. |
| 7,393,181 | B2 | 7/2008 | Mcbride et al. |
| 7,485,104 | B2 | 2/2009 | Kieval |
| 7,717,952 | B2 | 5/2010 | Case et al. |
| 7,744,642 | B2 | 6/2010 | Rittgers et al. |
| 7,762,941 | B2 | 7/2010 | Jarvik |
| 7,766,853 | B2 | 8/2010 | Lane |
| 7,766,892 | B2 | 8/2010 | Keren et al. |
| 7,766,961 | B2 | 8/2010 | Patel et al. |
| 7,780,628 | B1 | 8/2010 | Keren et al. |
| 7,811,221 | B2 | 10/2010 | Gross |
| 7,841,976 | B2 | 11/2010 | McBride et al. |
| 7,878,967 | B1 | 2/2011 | Khanal |
| 7,914,436 | B1 | 3/2011 | Kung |
| 7,914,503 | B2 | 3/2011 | Goodson et al. |
| 7,927,068 | B2 | 4/2011 | Mcbride et al. |
| 8,012,121 | B2 | 9/2011 | Goodson et al. |
| 8,079,948 | B2 | 12/2011 | Shifflette |
| 8,118,723 | B2 | 2/2012 | Richardson et al. |
| 8,123,669 | B2 | 2/2012 | Siess et al. |
| 8,157,758 | B2 | 4/2012 | Pecor et al. |
| 8,192,451 | B2 | 6/2012 | Cambronne et al. |
| 8,216,122 | B2 | 7/2012 | Kung |
| 8,221,492 | B2 | 7/2012 | Case et al. |
| 8,235,933 | B2 | 8/2012 | Keren et al. |
| 8,277,470 | B2 | 10/2012 | Demarais et al. |
| 8,376,707 | B2 | 2/2013 | Mcbride et al. |
| 8,439,859 | B2 | 5/2013 | Pfeffer et al. |
| 8,449,443 | B2 | 5/2013 | Rodefeld et al. |
| 8,485,961 | B2 | 7/2013 | Campbell et al. |
| 8,489,190 | B2 | 7/2013 | Pfeffer et al. |
| 8,512,262 | B2 | 8/2013 | Gertner |
| 8,535,211 | B2 | 9/2013 | Walters et al. |
| 8,538,535 | B2 | 9/2013 | Ariav et al. |
| 8,579,858 | B2 | 11/2013 | Reitan et al. |
| 8,591,393 | B2 | 11/2013 | Walters et al. |
| 8,591,539 | B2 | 11/2013 | Gellman |
| 8,597,170 | B2 | 12/2013 | Walters et al. |
| 8,617,239 | B2 | 12/2013 | Reitan |
| 8,672,868 | B2 | 3/2014 | Simons |

(56) References Cited

U.S. PATENT DOCUMENTS 8,684,904 B2 4/2014 Campbell et al.
8,690,749 B1 4/2014 Nunez
8,721,516 B2 5/2014 Scheckel
8,721,517 B2 5/2014 Zeng et al.
8,727,959 B2 5/2014 Reitan et al.
8,734,331 B2 5/2014 Evans et al.
8,734,508 B2 5/2014 Hastings et al.
8,777,832 B1 7/2014 Wang et al.
8,814,543 B2 8/2014 Liebing
8,814,776 B2 8/2014 Hastie et al.
8,814,933 B2 8/2014 Siess
8,827,887 B2 9/2014 Curtis et al.
8,849,398 B2 9/2014 Evans
8,864,642 B2 10/2014 Scheckel
8,888,728 B2 11/2014 Aboul-hosn et al.
8,900,060 B2 12/2014 Liebing
8,926,492 B2 1/2015 Scheckel
8,932,141 B2 1/2015 Liebing
8,944,748 B2 2/2015 Liebing
8,979,493 B2 3/2015 Roehn
8,992,163 B2 3/2015 Mcbride et al.
8,998,792 B2 4/2015 Scheckel
9,028,216 B2 5/2015 Schumacher et al.
9,067,006 B2 6/2015 Toellner
9,072,825 B2 7/2015 Pfeffer et al.
9,089,634 B2 7/2015 Schumacher et al.
9,138,518 B2 9/2015 Campbell et al.
9,162,017 B2 10/2015 Evans et al.
9,162,019 B2 10/2015 Horvath et al.
9,217,442 B2 12/2015 Wiessler et al.
9,259,521 B2 2/2016 Simons
9,278,189 B2 3/2016 Corbett
9,314,558 B2 4/2016 Er
9,327,067 B2 5/2016 Zeng et al.
9,328,741 B2 5/2016 Liebing
9,339,596 B2 5/2016 Roehn
9,345,824 B2 5/2016 Mohl et al.
9,358,329 B2 6/2016 Fitzgerald et al.
9,358,330 B2 6/2016 Schumacher
9,364,592 B2 6/2016 Mcbride et al.
9,364,593 B2 6/2016 Mcbride et al.
9,370,613 B2 6/2016 Hsu et al.
9,381,288 B2 7/2016 Schenck et al.
9,393,384 B1 7/2016 Kapur et al.
9,402,942 B2 8/2016 Hastie et al.
9,404,505 B2 8/2016 Scheckel
9,416,783 B2 8/2016 Schumacher et al.
9,416,791 B2 8/2016 Toellner
9,421,311 B2 8/2016 Tanner et al.
9,446,179 B2 9/2016 Keenan et al.
9,474,840 B2 10/2016 Siess
9,512,839 B2 12/2016 Liebing
9,533,082 B2 1/2017 Reichenbach et al.
9,533,084 B2 1/2017 Siess et al.
9,545,468 B2 1/2017 Aboul-hosn et al.
9,550,017 B2 1/2017 Spanier et al.
9,561,314 B2 2/2017 Aboul-hosn et al.
9,572,915 B2 2/2017 Heuring et al.
9,597,205 B2 3/2017 Tuval
9,597,437 B2 3/2017 Aboul-hosn et al.
9,603,983 B2 3/2017 Roehn et al.
9,611,743 B2 4/2017 Toellner et al.
9,616,159 B2 4/2017 Anderson et al.
9,623,161 B2 4/2017 Medvedev et al.
9,669,142 B2 6/2017 Spanier et al.
9,669,144 B2 6/2017 Spanier et al.
9,675,738 B2 6/2017 Tanner et al.
9,675,740 B2 6/2017 Zeng et al.
9,713,663 B2 7/2017 Medvedev et al.
9,717,833 B2 8/2017 Mcbride et al.
9,721,517 B2 8/2017 Namkung et al.
9,750,860 B2 9/2017 Schumacher
9,750,861 B2 9/2017 Hastie et al.
9,759,237 B2 9/2017 Liebing
9,764,113 B2 9/2017 Tuval et al.
9,771,801 B2 9/2017 Schumacher et al.
9,789,238 B2 10/2017 Aboul-hosn et al.
9,795,727 B2 10/2017 Schumacher
9,814,814 B2 11/2017 Corbett et al.
9,821,146 B2 11/2017 Tao et al.
9,827,356 B2 11/2017 Muller et al.
9,833,550 B2 12/2017 Siess
9,835,550 B2 12/2017 Kakuno et al.
9,850,906 B2 12/2017 Ozaki et al.
9,872,947 B2 1/2018 Keenan et al.
9,872,948 B2 1/2018 Siess
9,878,079 B2 1/2018 Pfeffer et al.
9,889,242 B2 2/2018 Pfeffer et al.
9,895,475 B2 2/2018 Toellner et al.
9,903,384 B2 2/2018 Roehn
9,907,890 B2 3/2018 Muller
9,907,891 B2 3/2018 Wiessler et al.
9,919,087 B2 3/2018 Pfeffer et al.
9,962,475 B2 5/2018 Campbell et al.
9,964,115 B2 5/2018 Scheckel
9,974,893 B2 5/2018 Toellner
9,999,714 B2 6/2018 Spanier et al.
10,029,037 B2 7/2018 Muller et al.
10,029,040 B2 7/2018 Taskin
10,039,872 B2 8/2018 Zeng et al.
10,039,874 B2 8/2018 Schwammenthal et al.
10,052,419 B2 8/2018 Er
10,052,420 B2 8/2018 Medvedev et al.
10,071,192 B2 9/2018 Zeng
10,086,121 B2 10/2018 Fitzgerald et al.
10,105,475 B2 10/2018 Muller
10,107,299 B2 10/2018 Scheckel
10,117,980 B2 11/2018 Keenan et al.
10,119,550 B2 11/2018 Bredenbreuker et al.
10,149,932 B2 12/2018 Mcbride et al.
10,172,985 B2 1/2019 Simon et al.
10,179,197 B2 1/2019 Kaiser et al.
10,183,104 B2 1/2019 Anderson et al.
10,196,899 B2 2/2019 Toellner et al.
10,207,037 B2 2/2019 Corbett et al.
10,208,763 B2 2/2019 Schumacher et al.
10,215,187 B2 2/2019 Mcbride et al.
10,221,866 B2 3/2019 Liebing
10,231,838 B2 3/2019 Chin et al.
10,232,099 B2 3/2019 Peters et al.
10,238,783 B2 3/2019 Aboul-hosn et al.
10,245,363 B1 4/2019 Rowe
10,265,447 B2 4/2019 Campbell et al.
10,265,448 B2 4/2019 Liebing
10,279,095 B2 5/2019 Aboul-hosn et al.
10,300,185 B2 5/2019 Aboul-hosn et al.
10,300,186 B2 5/2019 Aboul-hosn et al.
10,316,853 B2 6/2019 Toellner
10,322,175 B2 6/2019 Cully et al.
10,330,101 B2 6/2019 Toellner
10,342,904 B2 7/2019 Schumacher
10,342,906 B2 7/2019 D'ambrosio et al.
10,363,349 B2 7/2019 Muller et al.
10,369,260 B2 8/2019 Smith et al.
10,376,162 B2 8/2019 Edelman et al.
10,413,646 B2 9/2019 Wiessler et al.
10,449,276 B2 10/2019 Pfeffer et al.
10,449,279 B2 10/2019 Muller
10,478,538 B2 11/2019 Scheckel et al.
10,478,539 B2 11/2019 Pfeffer et al.
10,478,540 B2 11/2019 Scheckel et al.
10,495,101 B2 12/2019 Scheckel
10,557,475 B2 2/2020 Roehn
10,583,231 B2 3/2020 Schwammenthal et al.
10,584,589 B2 3/2020 Schumacher et al.
10,589,012 B2 3/2020 Toellner et al.
10,617,808 B2 4/2020 Hastie et al.
10,662,967 B2 5/2020 Scheckel
10,669,855 B2 6/2020 Toellner et al.
10,765,789 B2 9/2020 Zeng et al.
10,792,406 B2 10/2020 Roehn et al.
10,799,624 B2 10/2020 Pfeffer et al.
10,799,626 B2 10/2020 Siess et al.
10,801,511 B2 10/2020 Siess et al.

(56) References Cited

U.S. PATENT DOCUMENTS 10,806,838 B2 10/2020 Er
10,835,653 B2 11/2020 Liebing
10,842,922 B2 11/2020 Roehn et al.
10,857,272 B2 12/2020 Liebing
10,864,309 B2 12/2020 Mcbride et al.
10,864,310 B2 12/2020 Schwammenthal et al.
10,865,801 B2 12/2020 Mcbride et al.
10,874,783 B2 12/2020 Pfeffer et al.
10,881,770 B2 1/2021 Tuval et al.
10,881,845 B2 1/2021 Siess et al.
10,894,115 B2 1/2021 Pfeffer et al.
10,898,629 B2 1/2021 Siess et al.
10,907,646 B2 2/2021 Bredenbreuker et al.
10,920,596 B2 2/2021 Toellner et al.
10,926,013 B2 2/2021 Schumacher et al.
10,926,060 B2 2/2021 Stern et al.
10,935,038 B2 3/2021 Siess
10,980,927 B2 4/2021 Pfeffer et al.
10,994,120 B2 5/2021 Tuval et al.
11,007,350 B2 5/2021 Tao et al.
11,020,584 B2 6/2021 Siess et al.
11,027,114 B2 6/2021 D'ambrosio et al.
11,033,729 B2 6/2021 Scheckel et al.
11,040,187 B2 6/2021 Wiessler et al.
RE48,649 E 7/2021 Siess
11,077,294 B2 8/2021 Keenan et al.
11,107,626 B2 8/2021 Siess et al.
11,116,960 B2 9/2021 Simon et al.
11,123,539 B2 9/2021 Pfeffer et al.
11,129,978 B2 9/2021 Pfeffer et al.
11,167,124 B2 11/2021 Pfeffer et al.
11,168,705 B2 11/2021 Liebing
11,185,679 B2 11/2021 Tuval et al.
11,185,680 B2 11/2021 Tuval et al.
11,191,944 B2 12/2021 Tuval et al.
11,197,690 B2 12/2021 Fantuzzi et al.
11,219,755 B2 1/2022 Siess et al.
11,229,786 B2 1/2022 Zeng et al.
11,253,692 B2 2/2022 Schumacher
11,253,693 B2 2/2022 Pfeffer et al.
11,260,212 B2 3/2022 Tuval et al.
11,260,213 B2 3/2022 Zeng et al.
11,260,215 B2 3/2022 Scheckel et al.
11,266,824 B2 3/2022 Er
11,268,521 B2 3/2022 Toellner
11,273,301 B2 3/2022 Pfeffer et al.
11,278,711 B2 3/2022 Liebing
11,280,345 B2 3/2022 Bredenbreuker et al.
11,285,309 B2 3/2022 Tuval et al.
11,291,825 B2 4/2022 Tuval et al.
11,298,523 B2 4/2022 Tuval et al.
11,298,525 B2 4/2022 Jahangir
11,305,105 B2 4/2022 Corbett et al.
11,313,228 B2 4/2022 Schumacher et al.
11,338,124 B2 5/2022 Pfeffer et al.
11,351,358 B2 6/2022 Nix et al.
11,364,373 B2 6/2022 Corbett et al.
11,413,446 B2 8/2022 Siess et al.
11,421,701 B2 8/2022 Schumacher et al.
11,434,922 B2 9/2022 Roehn
11,471,663 B2 10/2022 Tuval et al.
11,708,833 B2 7/2023 Mcbride et al.
11,833,278 B2 12/2023 Siess et al.
11,839,754 B2 12/2023 Tuval et al.
11,883,274 B2 1/2024 Schwammenthal et al.
11,986,602 B2 5/2024 Corbett et al.
12,070,382 B2 8/2024 Goslau et al.
12,090,314 B2 * 9/2024 Tuval .................. A61M 60/414
12,127,820 B2 10/2024 Tuval et al.
12,220,570 B2 2/2025 Hildebrand et al.
12,329,957 B2 6/2025 Tuval et al.
2001/0031210 A1 10/2001 Antaki et al.
2001/0031981 A1 10/2001 Evans et al.
2001/0041934 A1 11/2001 Yamazaki et al.
2002/0107536 A1 8/2002 Hussein
2002/0151799 A1 10/2002 Pantages et al.
2003/0055486 A1 3/2003 Adams et al.
2003/0088310 A1 5/2003 Hansen et al.
2003/0100816 A1 5/2003 Siess
2003/0135086 A1 7/2003 Khaw et al.
2003/0149473 A1 8/2003 Chouinard et al.
2003/0171650 A1 9/2003 Tartaglia et al.
2003/0187322 A1 10/2003 Siess
2003/0208097 A1 11/2003 Aboul-hosn et al.
2004/0064090 A1 4/2004 Keren et al.
2004/0064091 A1 4/2004 Keren et al.
2004/0111006 A1 6/2004 Alferness et al.
2004/0116769 A1 6/2004 Jassawalla et al.
2004/0167415 A1 8/2004 Gelfand et al.
2004/0210236 A1 10/2004 Allers et al.
2004/0260389 A1 12/2004 Case et al.
2005/0033406 A1 2/2005 Barnhart et al.
2005/0049692 A1 3/2005 Numamoto et al.
2005/0079274 A1 4/2005 Palasis et al.
2005/0085848 A1 4/2005 Johnson et al.
2005/0107657 A1 5/2005 Carrier et al.
2005/0107870 A1 5/2005 Wang et al.
2005/0119682 A1 6/2005 Nguyen et al.
2005/0137680 A1 6/2005 Ortiz et al.
2005/0180854 A1 8/2005 Grabau et al.
2005/0250975 A1 11/2005 Carrier et al.
2006/0024182 A1 2/2006 Akdis et al.
2006/0062672 A1 3/2006 Mcbride et al.
2006/0064059 A1 3/2006 Gelfand et al.
2006/0106449 A1 5/2006 Ben
2006/0135961 A1 6/2006 Rosenman et al.
2006/0155322 A1 7/2006 Sater et al.
2006/0265051 A1 11/2006 Caro et al.
2007/0073271 A1 3/2007 Brucker et al.
2007/0100415 A1 5/2007 Licata et al.
2007/0100435 A1 5/2007 Case et al.
2007/0142729 A1 6/2007 Pfeiffer et al.
2007/0162103 A1 7/2007 Case et al.
2007/0208291 A1 9/2007 Patel
2007/0244550 A1 10/2007 Eidenschink
2007/0260327 A1 11/2007 Case et al.
2007/0282243 A1 12/2007 Pini et al.
2007/0282413 A1 12/2007 Tockman et al.
2007/0293808 A1 12/2007 Williams et al.
2008/0009668 A1 1/2008 Cohn
2008/0086027 A1 4/2008 Siess et al.
2008/0103591 A1 5/2008 Siess
2008/0114339 A1 5/2008 McBride et al.
2008/0114374 A1 5/2008 Soma et al.
2008/0132747 A1 6/2008 Shifflette
2008/0132748 A1 6/2008 Shifflette
2008/0140189 A1 6/2008 Nguyen et al.
2008/0154236 A1 6/2008 Elkins et al.
2008/0183280 A1 7/2008 Agnew et al.
2008/0219653 A1 9/2008 Shioda
2008/0306327 A1 12/2008 Shifflette
2008/0306328 A1 12/2008 Ercolani et al.
2009/0024157 A1 1/2009 Anukhin
2009/0024195 A1 1/2009 Rezai et al.
2009/0062597 A1 3/2009 Shifflette
2009/0093764 A1 4/2009 Pfeffer et al.
2009/0093796 A1 4/2009 Pfeffer et al.
2009/0264991 A1 10/2009 Paul et al.
2009/0287299 A1 11/2009 Tabor et al.
2009/0318857 A1 12/2009 Goodson et al.
2010/0030098 A1 2/2010 Fojtik
2010/0048793 A1 2/2010 Baekelandt et al.
2010/0049313 A1 2/2010 Alon et al.
2010/0076247 A1 3/2010 Zilbershlag et al.
2010/0130810 A1 5/2010 Mohl
2010/0152523 A1 6/2010 Macdonald et al.
2010/0185043 A1 7/2010 Woodard et al.
2010/0222632 A1 9/2010 Poirier
2010/0268017 A1 10/2010 Siess
2010/0285084 A1 11/2010 Yang et al.
2011/0004046 A1 1/2011 Campbell et al.
2011/0034874 A1 2/2011 Reitan et al.
2011/0106244 A1 5/2011 Ferrari et al.
2011/0112567 A1 5/2011 Lenker et al.

(56) References Cited

U.S. PATENT DOCUMENTS

| | | | |
|---|---|---|---|
| 2011/0144633 | A1 | 6/2011 | Govari |
| 2011/0152999 | A1 | 6/2011 | Hastings et al. |
| 2011/0190874 | A1 | 8/2011 | Celermajer et al. |
| 2011/0213408 | A1 | 9/2011 | Gross et al. |
| 2011/0230949 | A1 | 9/2011 | Haverkost et al. |
| 2011/0257462 | A1 | 10/2011 | Rodefeld et al. |
| 2011/0264075 | A1 | 10/2011 | Leung et al. |
| 2011/0282128 | A1 | 11/2011 | Reitan et al. |
| 2011/0282274 | A1 | 11/2011 | Fulton |
| 2011/0301662 | A1 | 12/2011 | Bar-yoseph et al. |
| 2012/0022579 | A1 | 1/2012 | Fulton |
| 2012/0059460 | A1 | 3/2012 | Reitan |
| 2012/0089047 | A1 | 4/2012 | Ryba et al. |
| 2012/0089225 | A1 | 4/2012 | Akkerman et al. |
| 2012/0093628 | A1 | 4/2012 | Liebing |
| 2012/0116382 | A1 | 5/2012 | Ku et al. |
| 2012/0130469 | A1 | 5/2012 | Cragg et al. |
| 2012/0143141 | A1 | 6/2012 | Verkaik et al. |
| 2012/0172654 | A1 | 7/2012 | Bates |
| 2012/0172655 | A1 | 7/2012 | Campbell et al. |
| 2012/0172656 | A1 | 7/2012 | Walters et al. |
| 2012/0178985 | A1 | 7/2012 | Walters et al. |
| 2012/0178986 | A1 | 7/2012 | Campbell et al. |
| 2012/0224970 | A1 | 9/2012 | Schumacher et al. |
| 2012/0234411 | A1 | 9/2012 | Scheckel |
| 2012/0237353 | A1 | 9/2012 | Schumacher et al. |
| 2012/0237357 | A1 | 9/2012 | Schumacher et al. |
| 2012/0245680 | A1 | 9/2012 | Masuzawa et al. |
| 2012/0303112 | A1 | 11/2012 | Armstrong et al. |
| 2012/0316586 | A1 | 12/2012 | Demarais et al. |
| 2012/0328460 | A1 | 12/2012 | Horvath et al. |
| 2013/0041202 | A1 | 2/2013 | Toellner |
| 2013/0046376 | A1 | 2/2013 | Hassan et al. |
| 2013/0053623 | A1 | 2/2013 | Evans et al. |
| 2013/0053732 | A1 | 2/2013 | Heuser |
| 2013/0060077 | A1 | 3/2013 | Liebing |
| 2013/0066140 | A1 | 3/2013 | Mcbride et al. |
| 2013/0079874 | A1 | 3/2013 | Doss et al. |
| 2013/0085318 | A1 | 4/2013 | Toellner |
| 2013/0085319 | A1 | 4/2013 | Evans et al. |
| 2013/0177407 | A1 | 7/2013 | Farineau et al. |
| 2013/0177409 | A1 | 7/2013 | Schumacher et al. |
| 2013/0177432 | A1 | 7/2013 | Toellner et al. |
| 2013/0237744 | A1 | 9/2013 | Pfeffer et al. |
| 2013/0245360 | A1 | 9/2013 | Schumacher |
| 2013/0253328 | A1 | 9/2013 | Zelenka et al. |
| 2013/0303830 | A1 | 11/2013 | Zeng et al. |
| 2013/0303831 | A1 | 11/2013 | Evans |
| 2013/0303969 | A1 | 11/2013 | Keenan et al. |
| 2013/0331639 | A1 | 12/2013 | Campbell et al. |
| 2014/0018840 | A1 | 1/2014 | Morgan et al. |
| 2014/0025041 | A1 | 1/2014 | Fukuoka et al. |
| 2014/0039375 | A1 | 2/2014 | Jimenez et al. |
| 2014/0107399 | A1 | 4/2014 | Spence |
| 2014/0128659 | A1 | 5/2014 | Heuring et al. |
| 2014/0255176 | A1 | 9/2014 | Bredenbreuker et al. |
| 2014/0275720 | A1 | 9/2014 | Ferrari |
| 2014/0275722 | A1 | 9/2014 | Zimmermann et al. |
| 2014/0276051 | A1 | 9/2014 | Hoffman |
| 2014/0350523 | A1 | 11/2014 | Dehdashtian et al. |
| 2015/0005570 | A1 | 1/2015 | Fritz et al. |
| 2015/0018597 | A1 | 1/2015 | Fierens et al. |
| 2015/0031937 | A1 | 1/2015 | Kearsley et al. |
| 2015/0051435 | A1 | 2/2015 | Siess et al. |
| 2015/0119633 | A1 | 4/2015 | Haselby et al. |
| 2015/0157777 | A1 | 6/2015 | Tuval et al. |
| 2015/0164372 | A1 | 6/2015 | Navab et al. |
| 2015/0164662 | A1 | 6/2015 | Tuval |
| 2015/0176582 | A1 | 6/2015 | Liebing |
| 2015/0258262 | A1 | 9/2015 | Pfeffer et al. |
| 2015/0290370 | A1 | 10/2015 | Crunkleton et al. |
| 2015/0290372 | A1 | 10/2015 | Muller et al. |
| 2015/0306291 | A1 | 10/2015 | Bonde et al. |
| 2015/0328382 | A1 | 11/2015 | Corbett et al. |
| 2015/0343136 | A1 | 12/2015 | Nitzan et al. |
| 2015/0343179 | A1 | 12/2015 | Schumacher et al. |
| 2015/0343186 | A1 | 12/2015 | Nitzan et al. |
| 2016/0022890 | A1 | 1/2016 | Schwammenthal et al. |
| 2016/0051741 | A1 | 2/2016 | Schwammenthal et al. |
| 2016/0053768 | A1 | 2/2016 | Schumacher et al. |
| 2016/0064117 | A1 | 3/2016 | Romero et al. |
| 2016/0106896 | A1 | 4/2016 | Pfeffer et al. |
| 2016/0129170 | A1 | 5/2016 | Siess |
| 2016/0136341 | A1 | 5/2016 | Pfeffer et al. |
| 2016/0136342 | A1 | 5/2016 | Pfeffer et al. |
| 2016/0136343 | A1 | 5/2016 | Anagnostopoulos |
| 2016/0144089 | A1 | 5/2016 | Woo et al. |
| 2016/0184500 | A1 | 6/2016 | Zeng |
| 2016/0206425 | A1 | 7/2016 | Madrid et al. |
| 2016/0213827 | A1 | 7/2016 | Tanner et al. |
| 2016/0256619 | A1 | 9/2016 | Throckmorton et al. |
| 2016/0256620 | A1 | 9/2016 | Scheckel et al. |
| 2016/0258248 | A1 | 9/2016 | MacDonald |
| 2016/0279310 | A1 | 9/2016 | Scheckel et al. |
| 2016/0303299 | A1 | 10/2016 | Muller |
| 2016/0331378 | A1 | 11/2016 | Nitzan et al. |
| 2016/0354525 | A1 | 12/2016 | Mcbride et al. |
| 2017/0007403 | A1 | 1/2017 | Wildhirt et al. |
| 2017/0014562 | A1 | 1/2017 | Liebing |
| 2017/0028115 | A1 | 2/2017 | Muller |
| 2017/0035954 | A1 | 2/2017 | Muller et al. |
| 2017/0049946 | A1 | 2/2017 | Kapur et al. |
| 2017/0071769 | A1 | 3/2017 | Mangiardi |
| 2017/0087286 | A1 | 3/2017 | Spanier et al. |
| 2017/0087288 | A1 | 3/2017 | Groß-hardt et al. |
| 2017/0100527 | A1 | 4/2017 | Schwammenthal et al. |
| 2017/0173237 | A1 | 6/2017 | Pfeifer et al. |
| 2017/0197021 | A1 | 7/2017 | Nitzan et al. |
| 2017/0215918 | A1 | 8/2017 | Tao et al. |
| 2017/0232168 | A1 | 8/2017 | Reichenbach et al. |
| 2017/0232171 | A1 | 8/2017 | Roehn et al. |
| 2017/0258981 | A1 | 9/2017 | Franano et al. |
| 2017/0274128 | A1 | 9/2017 | Tamburino et al. |
| 2017/0290964 | A1 | 10/2017 | Barry |
| 2017/0333067 | A1 | 11/2017 | Wilson |
| 2017/0333607 | A1 | 11/2017 | Zarins |
| 2017/0340787 | A1 | 11/2017 | Corbett et al. |
| 2017/0340791 | A1 | 11/2017 | Aboul-Hosn et al. |
| 2017/0348470 | A1 | 12/2017 | D'ambrosio et al. |
| 2018/0050139 | A1 | 2/2018 | Siess et al. |
| 2018/0050142 | A1 | 2/2018 | Siess et al. |
| 2018/0055979 | A1 | 3/2018 | Corbett et al. |
| 2018/0064861 | A1 | 3/2018 | Dur et al. |
| 2018/0064862 | A1 | 3/2018 | Keenan et al. |
| 2018/0078159 | A1 | 3/2018 | Edelman et al. |
| 2018/0080326 | A1 | 3/2018 | Schumacher et al. |
| 2018/0100507 | A1 | 4/2018 | Wu et al. |
| 2018/0104453 | A1 | 4/2018 | Tao et al. |
| 2018/0126130 | A1 | 5/2018 | Nitzan et al. |
| 2018/0149164 | A1 | 5/2018 | Siess |
| 2018/0149165 | A1 | 5/2018 | Siess et al. |
| 2018/0169312 | A1 | 6/2018 | Barry |
| 2018/0169313 | A1 | 6/2018 | Schwammenthal et al. |
| 2018/0207334 | A1 | 7/2018 | Siess |
| 2018/0228952 | A1 | 8/2018 | Pfeffer et al. |
| 2018/0228953 | A1 | 8/2018 | Siess et al. |
| 2018/0264182 | A1 | 9/2018 | Spanier et al. |
| 2018/0264183 | A1 | 9/2018 | Jahangir |
| 2018/0280598 | A1 | 10/2018 | Curran et al. |
| 2018/0289877 | A1 | 10/2018 | Schumacher et al. |
| 2018/0303990 | A1 | 10/2018 | Siess et al. |
| 2018/0303992 | A1 | 10/2018 | Taskin |
| 2018/0303993 | A1 | 10/2018 | Schwammenthal et al. |
| 2018/0311422 | A1 | 11/2018 | Greatrex et al. |
| 2018/0353667 | A1 | 12/2018 | Moyer et al. |
| 2019/0015570 | A1 | 1/2019 | Muller |
| 2019/0030228 | A1 | 1/2019 | Keenan et al. |
| 2019/0046702 | A1 | 2/2019 | Siess et al. |
| 2019/0060539 | A1 | 2/2019 | Siess et al. |
| 2019/0070345 | A1 | 3/2019 | Mcbride et al. |
| 2019/0076167 | A1 | 3/2019 | Fantuzzi et al. |
| 2019/0083690 | A1 | 3/2019 | Siess et al. |
| 2019/0093769 | A1 | 3/2019 | Lima Sarabanda et al. |
| 2019/0101130 | A1 | 4/2019 | Bredenbreuker et al. |

(56) References Cited

U.S. PATENT DOCUMENTS

2019/0105437 A1 4/2019 Siess et al.
2019/0117865 A1 4/2019 Walters et al.
2019/0134287 A1 5/2019 Demou
2019/0143018 A1 5/2019 Salahieh et al.
2019/0143019 A1 5/2019 Mehaffey et al.
2019/0170153 A1 6/2019 Scheckel
2019/0175802 A1 6/2019 Tuval et al.
2019/0175803 A1 6/2019 Pfeffer et al.
2019/0175805 A1 6/2019 Tuval et al.
2019/0175806 A1 6/2019 Tuval et al.
2019/0209753 A1 7/2019 Tuval et al.
2019/0209755 A1 7/2019 Nix et al.
2019/0209757 A1 7/2019 Tuval et al.
2019/0209758 A1 7/2019 Tuval et al.
2019/0211836 A1 7/2019 Schumacher et al.
2019/0216994 A1 7/2019 Pfeffer et al.
2019/0224391 A1 7/2019 Liebing
2019/0224392 A1 7/2019 Pfeffer et al.
2019/0224393 A1 7/2019 Pfeffer et al.
2019/0239998 A1 8/2019 Tuval et al.
2019/0262518 A1 8/2019 Molteni et al.
2019/0269840 A1 9/2019 Tuval et al.
2019/0274812 A1 9/2019 Groh et al.
2019/0275224 A1 9/2019 Hanson et al.
2019/0282741 A1 9/2019 Franano et al.
2019/0290817 A1 9/2019 Guo et al.
2019/0307561 A1 10/2019 Gosal et al.
2019/0316591 A1 10/2019 Toellner
2019/0321527 A1 10/2019 King et al.
2019/0321530 A1 10/2019 Cambronne et al.
2019/0321531 A1 10/2019 Cambronne et al.
2019/0328948 A1 10/2019 Salahieh et al.
2019/0336664 A1 11/2019 Liebing
2019/0344001 A1 11/2019 Salahieh et al.
2019/0351118 A1 11/2019 Graichen et al.
2019/0365975 A1 12/2019 Muller et al.
2020/0000542 A1 1/2020 McFall et al.
2020/0038567 A1 2/2020 Siess et al.
2020/0078506 A1 3/2020 Schwammenthal et al.
2020/0086022 A1 3/2020 El Katerji et al.
2020/0087199 A1 3/2020 Gimblet
2020/0093973 A1 3/2020 Gandhi et al.
2020/0114053 A1 4/2020 Salahieh et al.
2020/0155739 A1 5/2020 Siess et al.
2020/0197585 A1 6/2020 Scheckel et al.
2020/0237981 A1 7/2020 Tuval et al.
2020/0237982 A1 7/2020 Tuval et al.
2020/0237984 A1 7/2020 Tuval et al.
2020/0237985 A1 7/2020 Tuval et al.
2020/0237986 A1 7/2020 Tuval et al.
2020/0246527 A1 8/2020 Hildebrand et al.
2020/0268952 A1 8/2020 Nitzan et al.
2020/0276369 A1 9/2020 Nitzan et al.
2020/0276370 A1 9/2020 Keen et al.
2020/0288988 A1 9/2020 Goldvasser
2020/0289136 A1 9/2020 Chou et al.
2020/0376183 A1 12/2020 El Katerji et al.
2020/0405926 A1 12/2020 Alexander et al.
2021/0008261 A1 1/2021 Calomeni et al.
2021/0023285 A1 1/2021 Brandt
2021/0023286 A1 1/2021 Tuval et al.
2021/0038794 A1 2/2021 Tuval et al.
2021/0069394 A1 3/2021 Tuval et al.
2021/0069395 A1 3/2021 Tuval et al.
2021/0077676 A1 3/2021 Tuval et al.
2021/0077692 A1 3/2021 Tanner et al.
2021/0085955 A1 3/2021 Singru
2021/0121617 A1 4/2021 Harjes et al.
2021/0145475 A1 5/2021 Tao et al.
2021/0162199 A1 6/2021 Tuval et al.
2021/0170081 A1 6/2021 Kanz
2021/0178145 A1 6/2021 Tuval et al.
2021/0213273 A1 7/2021 Spanier et al.
2021/0236797 A1 8/2021 D'ambrosio et al.
2021/0260361 A1 8/2021 Charafeddine et al.
2021/0299433 A1 9/2021 Siess et al.
2022/0072297 A1 3/2022 Tuval et al.
2022/0079457 A1 3/2022 Tuval et al.
2022/0088368 A1 3/2022 Tuval et al.
2022/0134085 A1 5/2022 Siess et al.
2022/0161018 A1 5/2022 Mitze et al.
2022/0161019 A1 5/2022 Mitze et al.
2022/0161021 A1 5/2022 Mitze et al.
2022/0184376 A1 6/2022 Tuval et al.
2022/0226632 A1 7/2022 Tuval et al.
2022/0241574 A1 8/2022 Tuval et al.
2022/0249830 A1 8/2022 Kanz
2022/0313980 A1 10/2022 Hildebrand et al.
2022/0355096 A1 11/2022 Tuval et al.
2023/0001180 A1 1/2023 Boensch et al.
2023/0052997 A1 2/2023 Skrzypczak et al.
2023/0063196 A1 3/2023 Spanier et al.
2023/0071248 A1 3/2023 Keenan et al.
2023/0130285 A1 4/2023 Malone et al.
2023/0137473 A1 5/2023 Zipory et al.
2023/0211142 A1 7/2023 Gong
2023/0218887 A1 7/2023 Tuval et al.
2023/0226342 A1 7/2023 Tuval et al.
2023/0390545 A1 12/2023 D'Ambrosio et al.
2024/0189571 A1 6/2024 Tuval et al.
2024/0252812 A1 8/2024 Tuval et al.
2024/0261562 A1 8/2024 Tuval et al.
2024/0277997 A1 8/2024 Tuval et al.
2025/0387612 A1 12/2025 van Dort et al.

FOREIGN PATENT DOCUMENTS

CA 2701809 A1 4/2009
CA 2927346 A1 4/2009
CN 101448535 A 6/2009
CN 101820933 A 9/2010
CN 101854964 A 10/2010
CN 102365105 A 2/2012
CN 102805885 A 12/2012
CN 104185481 A 12/2014
CN 104703532 A 6/2015
CN 103182105 B 1/2016
CN 105214153 A 1/2016
CN 105682602 A 6/2016
CN 107050544 A 8/2017
CN 107137796 A 9/2017
CN 109069716 A 12/2018
CN 109641089 A 4/2019
CN 109821085 A 5/2019
CN 113457006 A 10/2021
CN 114259646 A 4/2022
CN 114588533 A 6/2022
CN 115040778 A 9/2022
CN 116036463 A 5/2023
CN 116328174 A 6/2023
CN 116474257 A 7/2023
CN 116867541 A 10/2023
DE 1033690 B 7/1958
DE 10336902 B3 8/2004
EP 0228787 A1 7/1987
EP 0256683 A2 2/1988
EP 0807447 A1 11/1997
EP 0916359 A1 5/1999
EP 1339443 A1 9/2003
EP 0925801 B1 11/2004
EP 1651290 A1 5/2006
EP 1827531 A1 9/2007
EP 1871441 A2 1/2008
EP 2047872 A1 4/2009
EP 2047873 A1 4/2009
EP 2109394 A2 10/2009
EP 2217300 A1 8/2010
EP 2218469 A1 8/2010
EP 2234658 A2 10/2010
EP 2282070 A1 2/2011
EP 2298374 A1 3/2011
EP 2299119 A1 3/2011
EP 2301598 A1 3/2011
EP 2308524 A1 4/2011

(56) References Cited

FOREIGN PATENT DOCUMENTS

| | | | |
|---|---|---|---|
| EP | 2314331 | A1 | 4/2011 |
| EP | 2345440 | A1 | 7/2011 |
| EP | 2366412 | A2 | 9/2011 |
| EP | 2376788 | A1 | 10/2011 |
| EP | 2408489 | A1 | 1/2012 |
| EP | 2424587 | A1 | 3/2012 |
| EP | 2475415 | A1 | 7/2012 |
| EP | 2607712 | A1 | 6/2013 |
| EP | 2040639 | B1 | 2/2014 |
| EP | 1207934 | B1 | 8/2014 |
| EP | 2662099 | B1 | 9/2014 |
| EP | 2427230 | B1 | 12/2014 |
| EP | 2396050 | B1 | 1/2015 |
| EP | 2835141 | A1 | 2/2015 |
| EP | 2840954 | A1 | 3/2015 |
| EP | 2841122 | A1 | 3/2015 |
| EP | 2841124 | A1 | 3/2015 |
| EP | 2860849 | A1 | 4/2015 |
| EP | 2868331 | A2 | 5/2015 |
| EP | 2868332 | A1 | 5/2015 |
| EP | 2999496 | A2 | 3/2016 |
| EP | 3000492 | A1 | 3/2016 |
| EP | 3000493 | A1 | 3/2016 |
| EP | 3055922 | A1 | 8/2016 |
| EP | 3062730 | A1 | 9/2016 |
| EP | 3115070 | A1 | 1/2017 |
| EP | 3127562 | A1 | 2/2017 |
| EP | 2922486 | B1 | 5/2017 |
| EP | 3216467 | A1 | 9/2017 |
| EP | 3222302 | A1 | 9/2017 |
| EP | 3236079 | A1 | 10/2017 |
| EP | 3287154 | A1 | 2/2018 |
| EP | 3287155 | A1 | 2/2018 |
| EP | 3326567 | A1 | 5/2018 |
| EP | 3329951 | A1 | 6/2018 |
| EP | 3338825 | A1 | 6/2018 |
| EP | 3205360 | B1 | 8/2018 |
| EP | 3359214 | A1 | 8/2018 |
| EP | 3359215 | A1 | 8/2018 |
| EP | 3398624 | A1 | 11/2018 |
| EP | 3398625 | A1 | 11/2018 |
| EP | 3407930 | A1 | 12/2018 |
| EP | 3446729 | A1 | 2/2019 |
| EP | 3446730 | A1 | 2/2019 |
| EP | 3545983 | A1 | 10/2019 |
| EP | 3606575 | A1 | 2/2020 |
| EP | 3698820 | A1 | 8/2020 |
| EP | 3737436 | A1 | 11/2020 |
| EP | 3782665 | A1 | 2/2021 |
| EP | 3848089 | A1 | 7/2021 |
| EP | 3858421 | A1 | 8/2021 |
| EP | 3897814 | A1 | 10/2021 |
| EP | 4218899 | A1 | 8/2023 |
| EP | 4252825 | A2 | 10/2023 |
| GB | 2239675 | A | 7/1991 |
| GB | 2451161 | A | 1/2009 |
| GB | 2504175 | A | 1/2014 |
| GB | 2504177 | A | 1/2014 |
| JP | 2003504091 | A | 2/2003 |
| JP | 2004202006 | A | 7/2004 |
| JP | 2008519624 | A | 6/2008 |
| JP | 4159781 | B2 | 10/2008 |
| JP | 2009530041 | A | 8/2009 |
| JP | 2012505038 | A | 3/2012 |
| JP | 2012527269 | A | 11/2012 |
| JP | 2015500666 | A | 1/2015 |
| JP | 2015516267 | A | 6/2015 |
| JP | 2016509950 | A | 4/2016 |
| JP | 2017196495 | A | 11/2017 |
| JP | 2018509223 | A | 4/2018 |
| JP | 2018528804 | A | 10/2018 |
| JP | 2018535727 | A | 12/2018 |
| JP | 2018536447 | A | 12/2018 |
| JP | 2020503083 | A | 1/2020 |
| JP | 2021510318 | A | 4/2021 |

| | | | |
|---|---|---|---|
| WO | 9001972 | A1 | 3/1990 |
| WO | 90/13321 | | 11/1990 |
| WO | 1994/01148 | A1 | 1/1994 |
| WO | 99/34847 | | 7/1999 |
| WO | 2001/083016 | A2 | 5/2000 |
| WO | 2000043053 | A1 | 7/2000 |
| WO | 0062838 | A2 | 10/2000 |
| WO | 2002/070039 | A2 | 3/2001 |
| WO | 2002/038085 | | 5/2002 |
| WO | 03/006096 | | 1/2003 |
| WO | 03/103745 | A2 | 12/2003 |
| WO | 2004073796 | A2 | 9/2004 |
| WO | 2005020848 | A2 | 3/2005 |
| WO | 2007081818 | A2 | 7/2007 |
| WO | 2007112033 | A2 | 10/2007 |
| WO | 2007127477 | A2 | 11/2007 |
| WO | 2008005747 | A2 | 1/2008 |
| WO | 2008005990 | A2 | 1/2008 |
| WO | 2008055301 | A1 | 5/2008 |
| WO | 2008104858 | A2 | 9/2008 |
| WO | 2009010963 | A2 | 1/2009 |
| WO | 2009046096 | A1 | 4/2009 |
| WO | 2009046790 | A2 | 4/2009 |
| WO | 2009064879 | A2 | 5/2009 |
| WO | 2009129481 | A1 | 10/2009 |
| WO | 2010042546 | | 4/2010 |
| WO | 2010063494 | A1 | 6/2010 |
| WO | 2010105854 | A1 | 9/2010 |
| WO | 2010127871 | A1 | 11/2010 |
| WO | 2010133567 | A1 | 11/2010 |
| WO | 2010150208 | A2 | 12/2010 |
| WO | 2011035926 | A1 | 3/2011 |
| WO | 2011047884 | A1 | 4/2011 |
| WO | 2011076441 | A1 | 6/2011 |
| WO | 2011089022 | A1 | 7/2011 |
| WO | 2011160858 | A1 | 12/2011 |
| WO | 2012007141 | A1 | 1/2012 |
| WO | 2012094535 | A2 | 7/2012 |
| WO | 2013032849 | A1 | 3/2013 |
| WO | 2013070186 | A1 | 5/2013 |
| WO | 2013093001 | A2 | 6/2013 |
| WO | 2013119752 | A2 | 8/2013 |
| WO | 2013148697 | A1 | 10/2013 |
| WO | 2013173239 | A1 | 11/2013 |
| WO | 2013183060 | A2 | 12/2013 |
| WO | 2014063119 | A1 | 4/2014 |
| WO | 2014141284 | A2 | 9/2014 |
| WO | 2014164292 | A1 | 10/2014 |
| WO | 2015063277 | A2 | 5/2015 |
| WO | 2015160943 | A1 | 10/2015 |
| WO | 2015177793 | A2 | 11/2015 |
| WO | 2016001218 | A1 | 1/2016 |
| WO | 2016005803 | A2 | 1/2016 |
| WO | 2016185473 | A1 | 11/2016 |
| WO | 2016207293 | A1 | 12/2016 |
| WO | 2017032751 | A1 | 3/2017 |
| WO | 2017053361 | A1 | 3/2017 |
| WO | 2017060254 | A1 | 4/2017 |
| WO | 2017081561 | A1 | 5/2017 |
| WO | 2017137604 | A1 | 8/2017 |
| WO | 2017147291 | A1 | 8/2017 |
| WO | 2017159849 | A1 | 9/2017 |
| WO | 2017162618 | A1 | 9/2017 |
| WO | 2017196271 | A1 | 11/2017 |
| WO | 2018033920 | A1 | 2/2018 |
| WO | 2018036927 | A1 | 3/2018 |
| WO | 2018045299 | A1 | 3/2018 |
| WO | 2018061001 | A2 | 4/2018 |
| WO | 2018061002 | A1 | 4/2018 |
| WO | 2018067410 | A1 | 4/2018 |
| WO | 2018078615 | A1 | 5/2018 |
| WO | 2018096531 | A1 | 5/2018 |
| WO | 2018158636 | A1 | 9/2018 |
| WO | 2018172848 | A2 | 9/2018 |
| WO | 2018220589 | A1 | 12/2018 |
| WO | 2018226991 | A1 | 12/2018 |
| WO | 2018234454 | A1 | 12/2018 |
| WO | 2019079342 | A1 | 4/2019 |
| WO | 2019094963 | A1 | 5/2019 |

(56) References Cited

FOREIGN PATENT DOCUMENTS

| | | | |
|---|---|---|---|
| WO | 2019125899 | A1 | 6/2019 |
| WO | 2019138350 | A2 | 7/2019 |
| WO | 2019152875 | A1 | 8/2019 |
| WO | 2019158996 | A1 | 8/2019 |
| WO | 2019229223 | A1 | 12/2019 |
| WO | 2020152611 | A2 | 7/2020 |
| WO | 2021055826 | A1 | 3/2021 |
| WO | 2021062265 | A1 | 4/2021 |
| WO | 2021152012 | A1 | 8/2021 |
| WO | 2021159147 | A1 | 8/2021 |
| WO | 2021198881 | A1 | 10/2021 |
| WO | 2021205346 | A2 | 10/2021 |
| WO | 2022189932 | A1 | 9/2022 |
| WO | 2023014742 | A1 | 2/2023 |
| WO | 2023062453 | A1 | 4/2023 |
| WO | 2024057252 | A1 | 3/2024 |
| WO | 2024057253 | A2 | 3/2024 |
| WO | 2024057254 | A1 | 3/2024 |
| WO | 2024057255 | A2 | 3/2024 |
| WO | 2024057256 | A2 | 3/2024 |
| WO | 2024057257 | A2 | 3/2024 |
| WO | 2025141457 | A1 | 7/2025 |
| WO | 2025141460 | A1 | 7/2025 |
| WO | 2025141461 | A2 | 7/2025 |

OTHER PUBLICATIONS

Corrected Notice of Allowance for U.S. Appl. No. 16/279,352 mailed Nov. 3, 2021.
Corrected Notice of Allowance for U.S. Appl. No. 16/281,237 mailed Mar. 31, 2021.
Corrected Notice of Allowance for U.S. Appl. No. 16/810,116 mailed Apr. 7, 2023.
Corrected Notice of Allowance for U.S. Appl. No. 16/810,121 mailed Jun. 28, 2022.
Corrected Notice of Allowance for U.S. Appl. No. 16/810,121 mailed Sep. 20, 2022.
Corrected Notice of Allowance for U.S. Appl. No. 16/810,172 mailed Feb. 2, 2022.
Corrected Notice of Allowance for U.S. Appl. No. 16/952,389 mailed Feb. 20, 2024.
Corrected Notice of Allowance for U.S. Appl. No. 16/952,389 mailed Mar. 4, 2024.
Corrected Notice of Allowance for U.S. Appl. No. 16/952,444 mailed Mar. 13, 2024.
Corrected Notice of Allowance for U.S. Appl. No. 17/069,570 mailed Apr. 10, 2024.
Corrected Notice of Allowance for U.S. Appl. No. 17/070,323 mailed Jun. 1, 2023.
Corrected Notice of Allowance for U.S. Appl. No. 17/070,323 mailed Oct. 4, 2023.
Corrected Notice of Allowance for U.S. Appl. No. 17/077,769 mailed Nov. 15, 2023.
Corrected Notice of Allowance for U.S. Appl. No. 17/077,769 mailed Nov. 6, 2023.
Corrected Notice of Allowance for U.S. Appl. No. 17/077,769 mailed Oct. 4, 2023.
Corrected Notice of Allowance for U.S. Appl. No. 17/180,041 mailed Jun. 30, 2023.
Corrected Notice of Allowance for U.S. Appl. No. 17/180,041 mailed Oct. 4, 2023.
Corrected Notice of Allowance for U.S. Appl. No. 17/182,482 mailed Feb. 7, 2023.
Examination Report for Australian Patent Application No. 2017349920 mailed Jun. 2, 2022.
Examination Report for Australian Patent Application No. 2017349920 mailed Nov. 4, 2022.
Examination Report for Australian Patent Application No. 2019206421 mailed Sep. 29, 2023.
Examination Report for European Application No. 21158196.2 mailed May 28, 2024.
Examination Report for European Application No. 21718229.4 mailed Mar. 17, 2022.
Examination Report for Indian Patent Application No. 201917018651 mailed Jun. 30, 2021.
Examination Report for Indian Patent Application No. 202047017397 mailed May 4, 2022.
Examination Report for Indian Patent Application No. 202147033522 mailed May 24, 2023.
Extended Search Report and Preliminary Opinion for European Application No. 23159720.4 mailed Jun. 27, 2023.
Extended Search Report for European Application No. 19172327.9 mailed Aug. 23, 2019.
Extended Search Report for European Application No. 20159714.3 mailed Jul. 3, 2020.
Extended Search Report for European Application No. 20159716.8 mailed Jul. 3, 2020.
Extended Search Report for European Application No. 20159718.4 mailed Jul. 9, 2020.
Extended Search Report for European Application No. 20195082.1 mailed Nov. 5, 2020.
Extended Search Report for European Application No. 20195084.7 mailed Nov. 5, 2020.
Extended Search Report for European Application No. 20195085.4 mailed Nov. 4, 2020.
Extended Search Report for European Application No. 20195987.1 mailed Nov. 5, 2020.
Extended Search Report for European Application No. 21156647.6 mailed May 21, 2021.
Extended Search Report for European Application No. 21158196.2 mailed Apr. 8, 2021.
Extended Search Report for European Application No. 21158902.3 mailed Apr. 29, 2021.
Extended Search Report for European Application No. 21158903.1 mailed Apr. 9, 2021.
Extended Search Report for European Application No. 21208803.3 mailed Apr. 13, 2022.
Extended Search Report for European Application No. 21209256.3 mailed Mar. 2, 2022.
Extended Search Report for European Application No. 22155936.2 mailed Jul. 8, 2022.
Extended Search Report for European Application No. 22163640.0 mailed Jun. 29, 2022.
Extended Search Report for European Application No. 22163648.3 mailed Aug. 10, 2022.
Extended Search Report for European Application No. 22163653.3 mailed Jul. 1, 2022.
Extended Search Report for European Application No. 22197511.3 mailed Dec. 5, 2022.
Extended Search Report for European Application No. 23159721.2 mailed Jun. 26, 2023.
Extended Search Report for European Application No. 23159724.6 mailed Jun. 26, 2023.
Extended Search Report for European Application No. 23159725.3 mailed Jun. 28, 2023.
Extended Search Report for European Application No. 23189145.8 mailed Nov. 27, 2023.
Extended Search Report for European Application No. 23189147.4 mailed Dec. 13, 2023.
Extended Search Report for European Application No. 23189148.2 mailed Dec. 13, 2023.
Extended Search Report for European Application No. 23189149.0 mailed Dec. 13, 2023.
Final Office Action for U.S. Appl. No. 16/275,559 mailed Jan. 4, 2021.
Final Office Action for U.S. Appl. No. 16/275,559 mailed May 17, 2022.
Final Office Action for U.S. Appl. No. 16/275,559 mailed Oct. 20, 2021.
Final Office Action for U.S. Appl. No. 16/276,965 mailed Apr. 13, 2021.

(56) References Cited

OTHER PUBLICATIONS

Final Office Action for U.S. Appl. No. 16/277,411 mailed Jun. 21, 2021.
Final Office Action for U.S. Appl. No. 16/279,352 mailed May 3, 2021.
Final Office Action for U.S. Appl. No. 16/952,327 mailed Jun. 8, 2023.
Final Office Action for U.S. Appl. No. 16/952,389 mailed Jul. 18, 2023.
Final Office Action for U.S. Appl. No. 16/952,444 mailed Jul. 5, 2023.
Final Office Action for U.S. Appl. No. 17/069,064 mailed May 25, 2022.
Final Office Action for U.S. Appl. No. 17/069,570 mailed Apr. 28, 2023.
Final Office Action for U.S. Appl. No. 17/070,670 mailed Jun. 2, 2023.
Final Office Action for U.S. Appl. No. 17/077,769 mailed Jun. 7, 2023.
Final Office Action for U.S. Appl. No. 17/078,472 mailed Oct. 23, 2023.
Final Office Action for U.S. Appl. No. 17/176,344 mailed Apr. 12, 2024.
Final Office Action for U.S. Appl. No. 17/176,344 mailed Oct. 12, 2022.
Final Office Action for U.S. Appl. No. 17/528,807 mailed Apr. 24, 2024.
Final Office Action for U.S. Appl. No. 17/574,701 mailed Feb. 8, 2024.
Hearing Notice for Indian Patent Application No. 201917018651 mailed Dec. 11, 2023.
International Search Report and Written Opinion from International Application No. PCT/IB2019/050186 mailed Jul. 18, 2019.
International Search Report and Written Opinion from International Application No. PCT/IB2020/050515 mailed Sep. 9, 2020.
International Search Report and Written Opinion from International Application No. PCT/IB2021/052590 mailed Sep. 14, 2021.
International Search Report and Written Opinion from International Application No. PCT/IB2021/052857 mailed Oct. 5, 2021.
International Search Report and Written Opinion from International Application No. PCT/IB2022/051990 mailed Aug. 10, 2022.
International Search Report and Written Opinion from International Application No. PCT/IB2022/058101 mailed Feb. 20, 2023.
International Search Report and Written Opinion from International Application No. PCT/IB2023/059136 mailed Jan. 2, 2024.
International Search Report and Written Opinion from International Application No. PCT/IB2023/059137 mailed Mar. 21, 2024.
International Search Report and Written Opinion from International Application No. PCT/IB2023/059138 mailed Feb. 7, 2024.
International Search Report and Written Opinion from International Application No. PCT/IB2023/059141 mailed Mar. 22, 2024.
International Search Report and Written Opinion from International Application No. PCT/IB2023/059142 mailed Apr. 16, 2024.
International Search Report and Written Opinion from International Application No. PCT/IB2023/059143 mailed Mar. 14, 2024.
International Search Report and Written Opinion from International Application No. PCT/IL2017/051158 mailed Jan. 17, 2018.
Invitation to Pay Additional Fees for International Application No. PCT/IB2020/050515 mailed Mar. 31, 2020.
Invitation to Pay Additional Fees for International Application No. PCT/IB2021/052590 mailed Jul. 23, 2021.
Invitation to Pay Additional Fees for International Application No. PCT/IB2021/052857 mailed Jul. 7, 2021.
Invitation to Pay Additional Fees for International Application No. PCT/IB2022/051990 mailed May 13, 2022.
Invitation to Pay Additional Fees for International Application No. PCT/IB2023/059134 mailed Dec. 21, 2023.
Invitation to Pay Additional Fees for International Application No. PCT/IB2023/059137 mailed Jan. 2, 2024.
Invitation to Pay Additional Fees for International Application No. PCT/IB2023/059138 mailed Dec. 8, 2023.
Invitation to Pay Additional Fees for International Application No. PCT/IB2023/059141 mailed Dec. 22, 2023.
Invitation to Pay Additional Fees for International Application No. PCT/IB2023/059142 mailed Jan. 2, 2024.
Issue Notification for U.S. Appl. No. 16/275,559 mailed Nov. 22, 2023.
Issue Notification for U.S. Appl. No. 16/276,965 mailed Mar. 16, 2022.
Issue Notification for U.S. Appl. No. 16/277,411 mailed Feb. 9, 2022.
Issue Notification for U.S. Appl. No. 16/278,482 mailed Jan. 13, 2021.
Issue Notification for U.S. Appl. No. 16/279,352 mailed Nov. 10, 2021.
Issue Notification for U.S. Appl. No. 16/280,566 mailed Nov. 10, 2021.
Issue Notification for U.S. Appl. No. 16/281,237 mailed Apr. 14, 2021.
Issue Notification for U.S. Appl. No. 16/281,264 mailed Dec. 16, 2020.
Issue Notification for U.S. Appl. No. 16/750,354 mailed Nov. 17, 2021.
Issue Notification for U.S. Appl. No. 16/810,086 mailed Mar. 9, 2022.
Issue Notification for U.S. Appl. No. 16/810,116 mailed May 17, 2023.
Issue Notification for U.S. Appl. No. 16/810,172 mailed Mar. 23, 2022.
Issue Notification for U.S. Appl. No. 16/810,270 mailed Oct. 12, 2022.
Issue Notification for U.S. Appl. No. 16/952,389 mailed Mar. 13, 2024.
Issue Notification for U.S. Appl. No. 16/952,444 mailed Mar. 20, 2024.
Issue Notification for U.S. Appl. No. 17/069,321 mailed Mar. 16, 2022.
Issue Notification for U.S. Appl. No. 17/070,323 mailed Oct. 18, 2023.
Issue Notification for U.S. Appl. No. 17/077,769 mailed Nov. 29, 2023.
Issue Notification for U.S. Appl. No. 17/078,439 mailed Apr. 3, 2024.
Issue Notification for U.S. Appl. No. 17/173,944 mailed Jun. 12, 2024.
Issue Notification for U.S. Appl. No. 17/177,296 mailed Mar. 13, 2024.
Issue Notification for U.S. Appl. No. 17/180,041 mailed Oct. 18, 2023.
Non-Final Office Action for U.S. Appl. No. 16/275,559 mailed Jan. 19, 2023.
Non-Final Office Action for U.S. Appl. No. 16/275,559 mailed Jan. 26, 2022.
Non-Final Office Action for U.S. Appl. No. 16/275,559 mailed May 26, 2021.
Non-Final Office Action for U.S. Appl. No. 16/275,559 mailed Sep. 4, 2020.
Non-Final Office Action for U.S. Appl. No. 16/276,965 mailed Jul. 26, 2021.
Non-Final Office Action for U.S. Appl. No. 16/276,965 mailed Jun. 19, 2020.
Non-Final Office Action for U.S. Appl. No. 16/276,965 mailed Nov. 30, 2020.
Non-Final Office Action for U.S. Appl. No. 16/277,411 mailed Feb. 9, 2021.
Non-Final Office Action for U.S. Appl. No. 16/278,482 mailed Jun. 23, 2020.
Non-Final Office Action for U.S. Appl. No. 16/279,352 mailed Nov. 10, 2020.
Non-Final Office Action for U.S. Appl. No. 16/280,566 mailed Dec. 21, 2020.

(56) References Cited

OTHER PUBLICATIONS

Non-Final Office Action for U.S. Appl. No. 16/281,237 mailed Aug. 21, 2020.
Non-Final Office Action for U.S. Appl. No. 16/281,264 mailed Jun. 29, 2020.
Non-Final Office Action for U.S. Appl. No. 16/810,121 mailed Mar. 9, 2022.
Non-Final Office Action for U.S. Appl. No. 16/952,327 mailed Nov. 8, 2022.
Non-Final Office Action for U.S. Appl. No. 16/952,327 mailed Oct. 13, 2023.
Non-Final Office Action for U.S. Appl. No. 16/952,389 mailed Dec. 21, 2022.
Non-Final Office Action for U.S. Appl. No. 16/952,444 mailed Jan. 6, 2023.
Non-Final Office Action for U.S. Appl. No. 17/069,064 mailed Dec. 9, 2021.
Non-Final Office Action for U.S. Appl. No. 17/069,064 mailed Nov. 7, 2022.
Non-Final Office Action for U.S. Appl. No. 17/069,321 mailed Nov. 18, 2021.
Non-Final Office Action for U.S. Appl. No. 17/069,570 mailed Oct. 2, 2023.
Non-Final Office Action for U.S. Appl. No. 17/069,570 mailed Oct. 6, 2022.
Non-Final Office Action for U.S. Appl. No. 17/070,323 mailed Oct. 6, 2022.
Non-Final Office Action for U.S. Appl. No. 17/070,670 mailed Oct. 30, 2023.
Non-Final Office Action for U.S. Appl. No. 17/070,670 mailed Oct. 5, 2022.
Non-Final Office Action for U.S. Appl. No. 17/077,769 mailed Oct. 5, 2022.
Non-Final Office Action for U.S. Appl. No. 17/078,439 mailed Jun. 1, 2023.
Non-Final Office Action for U.S. Appl. No. 17/078,472 mailed Feb. 14, 2024.
Non-Final Office Action for U.S. Appl. No. 17/078,472 mailed May 4, 2023.
Non-Final Office Action for U.S. Appl. No. 17/176,344 mailed Apr. 20, 2022.
Non-Final Office Action for U.S. Appl. No. 17/176,344 mailed Oct. 31, 2023.
Non-Final Office Action for U.S. Appl. No. 17/180,041 mailed Jan. 31, 2023.
Non-Final Office Action for U.S. Appl. No. 17/528,807 mailed Jan. 12, 2024.
Non-Final Office Action for U.S. Appl. No. 17/574,701 mailed Sep. 27, 2023.
Non-Final Office Action for U.S. Appl. No. 17/609,589 mailed Jul. 1, 2024.
Notice of Allowance for U.S. Appl. No. 16/275,559 mailed Jul. 27, 2023.
Notice of Allowance for U.S. Appl. No. 16/275,559 mailed Oct. 4, 2023.
Notice of Allowance for U.S. Appl. No. 16/276,965 mailed Jan. 26, 2022.
Notice of Allowance for U.S. Appl. No. 16/277,411 mailed Dec. 8, 2021.
Notice of Allowance for U.S. Appl. No. 16/278,482 mailed Dec. 2, 2020.
Notice of Allowance for U.S. Appl. No. 16/279,352 mailed Oct. 1, 2021.
Notice of Allowance for U.S. Appl. No. 16/280,566 mailed Aug. 31, 2021.
Notice of Allowance for U.S. Appl. No. 16/281,237 mailed Feb. 1, 2021.
Notice of Allowance for U.S. Appl. No. 16/281,264 mailed Nov. 12, 2020.
Notice of Allowance for U.S. Appl. No. 16/750,354 mailed Oct. 18, 2021.
Notice of Allowance for U.S. Appl. No. 16/810,086 mailed Jan. 7, 2022.
Notice of Allowance for U.S. Appl. No. 16/810,116 mailed Mar. 13, 2023.
Notice of Allowance for U.S. Appl. No. 16/810,121 mailed Aug. 19, 2022.
Notice of Allowance for U.S. Appl. No. 16/810,121 mailed Jun. 1, 2022.
Notice of Allowance for U.S. Appl. No. 16/810,172 mailed Jan. 10, 2022.
Notice of Allowance for U.S. Appl. No. 16/810,270 mailed Apr. 14, 2022.
Notice of Allowance for U.S. Appl. No. 16/810,270 mailed Jul. 22, 2022.
Notice of Allowance for U.S. Appl. No. 16/952,327 mailed Apr. 29, 2024.
Notice of Allowance for U.S. Appl. No. 16/952,389 mailed Feb. 7, 2024.
Notice of Allowance for U.S. Appl. No. 16/952,444 mailed Feb. 15, 2024.
Notice of Allowance for U.S. Appl. No. 17/069,064 mailed Mar. 8, 2023.
Notice of Allowance for U.S. Appl. No. 17/069,321 mailed Feb. 2, 2022.
Notice of Allowance for U.S. Appl. No. 17/069,570 mailed Jun. 24, 2024.
Notice of Allowance for U.S. Appl. No. 17/069,570 mailed Mar. 13, 2024.
Notice of Allowance for U.S. Appl. No. 17/070,323 mailed Aug. 30, 2023.
Notice of Allowance for U.S. Appl. No. 17/070,323 mailed May 15, 2023.
Notice of Allowance for U.S. Appl. No. 17/070,670 mailed Jun. 13, 2024.
Notice of Allowance for U.S. Appl. No. 17/077,769 mailed Sep. 27, 2023.
Notice of Allowance for U.S. Appl. No. 17/078,439 mailed Dec. 5, 2023.
Notice of Allowance for U.S. Appl. No. 17/078,439 mailed Feb. 27, 2024.
Notice of Allowance for U.S. Appl. No. 17/173,944 mailed Jul. 10, 2023.
Notice of Allowance for U.S. Appl. No. 17/173,944 mailed Mar. 6, 2024.
Notice of Allowance for U.S. Appl. No. 17/173,944 mailed Nov. 8, 2023.
Notice of Allowance for U.S. Appl. No. 17/177,296 mailed Feb. 14, 2024.
Notice of Allowance for U.S. Appl. No. 17/177,296 mailed Nov. 17, 2023.
Notice of Allowance for U.S. Appl. No. 17/180,041 mailed Jun. 13, 2023.
Notice of Allowance for U.S. Appl. No. 17/180,041 mailed Sep. 18, 2023.
Notice of Allowance for U.S. Appl. No. 17/182,482 mailed Apr. 21, 2023.
Notice of Allowance for U.S. Appl. No. 17/182,482 mailed Jan. 5, 2023.
Notice of Allowance for U.S. Appl. No. 17/574,701 mailed Jun. 26, 2024.
Notice of Missing Requirements for U.S. Appl. No. 18/447,025 mailed Feb. 1, 2024.
Office Action for Canadian Application No. 3,039,285 mailed Mar. 24, 2023.
Office Action for Canadian Application No. 3,080,800 mailed Sep. 12, 2023.
Office Action for Canadian Application No. 3,122,415 mailed Mar. 31, 2023.
Office Action for Canadian Application No. 3,176,272 mailed Jan. 2, 2024.

(56) References Cited

OTHER PUBLICATIONS

Office Action for Chinese Application No. 201780066201.3 mailed Jun. 29, 2021.
Office Action for Chinese Application No. 201980007116.9 mailed Nov. 28, 2022.
Office Action for Chinese Application No. 202080017728.9 mailed Nov. 6, 2023.
Office Action for Japanese Application No. 2019-521643 mailed Apr. 11, 2023.
Office Action for Japanese Application No. 2019-521643 mailed May 10, 2022.
Office Action for Japanese Application No. 2019-521643 mailed Oct. 27, 2022.
Office Action for Japanese Application No. 2019-521643 mailed Sep. 28, 2021.
Office Action for Japanese Application No. 2020-537746 mailed Feb. 21, 2023.
Office Action for Japanese Application No. 2021-533242 mailed Nov. 8, 2023.
Restriction Requirement for U.S. Appl. No. 16/275,559 mailed Jun. 2, 2020.
Restriction Requirement for U.S. Appl. No. 16/279,352 mailed Aug. 11, 2020.
Restriction Requirement for U.S. Appl. No. 16/280,566 mailed Aug. 11, 2020.
Restriction Requirement for U.S. Appl. No. 16/810,116 mailed Jun. 29, 2022.
Supplemental Notice of Allowability for U.S. Appl. No. 16/276,965 mailed Mar. 10, 2022.
Supplemental Notice of Allowability for U.S. Appl. No. 16/276,965 mailed Mar. 2, 2022.
Supplemental Notice of Allowability for U.S. Appl. No. 16/278,482 mailed Dec. 24, 2020.
Supplemental Notice of Allowability for U.S. Appl. No. 16/279,352 mailed Oct. 21, 2021.
Third Party Submission received during the prosecution of U.S. Appl. No. 17/078,439 on Sep. 28, 2022.
U.S. Appl. No. 14/567,439, filed Dec. 11, 2014.
U.S. Appl. No. 16/275,559, filed Feb. 14, 2019.
U.S. Appl. No. 16/276,965, filed Feb. 15, 2019.
U.S. Appl. No. 16/277,411, filed Feb. 15, 2019.
U.S. Appl. No. 16/278,482, filed Feb. 18, 2019.
U.S. Appl. No. 16/279,352, filed Feb. 19, 2019.
U.S. Appl. No. 16/280,566, filed Feb. 20, 2019.
U.S. Appl. No. 16/281,237, filed Feb. 21, 2019.
U.S. Appl. No. 16/281,264, filed Feb. 21, 2019.
U.S. Appl. No. 16/750,354, filed Jan. 23, 2020.
U.S. Appl. No. 16/810,086, filed Mar. 5, 2020.
U.S. Appl. No. 16/810,121, filed Mar. 5, 2020.
U.S. Appl. No. 16/952,327, filed Nov. 19, 2020.
U.S. Appl. No. 16/952,389, filed Nov. 19, 2020.
U.S. Appl. No. 16/952,444, filed Nov. 19, 2020.
U.S. Appl. No. 17/069,064, filed Oct. 13, 2020.
U.S. Appl. No. 17/069,321, filed Oct. 13, 2020.
U.S. Appl. No. 17/069,570, filed Oct. 13, 2020.
U.S. Appl. No. 17/070,323, filed Oct. 14, 2020.
U.S. Appl. No. 17/070,670, filed Oct. 14, 2020.
U.S. Appl. No. 17/077,769, filed Oct. 22, 2020.
U.S. Appl. No. 17/078,439, filed Oct. 23, 2020.
U.S. Appl. No. 17/078,472, filed Oct. 23, 2020.
U.S. Appl. No. 17/176,344, filed Feb. 16, 2021.
U.S. Appl. No. 17/177,296, filed Feb. 17, 2021.
U.S. Appl. No. 17/180,041, filed Feb. 19, 2021.
U.S. Appl. No. 17/182,482, filed Feb. 23, 2021.
U.S. Appl. No. 17/528,015, filed Nov. 16, 2021.
U.S. Appl. No. 17/528,807, filed Nov. 17, 2021.
U.S. Appl. No. 17/532,318, filed Nov. 22, 2021.
U.S. Appl. No. 17/574,701, filed Jan. 13, 2022.
U.S. Appl. No. 17/609,589, filed Nov. 8, 2021.
U.S. Appl. No. 17/677,571, filed Feb. 22, 2022.
U.S. Appl. No. 17/678,122, filed Feb. 23, 2022.
U.S. Appl. No. 17/857,402, filed Jul. 5, 2022.
U.S. Appl. No. 18/121,995, filed Mar. 15, 2023.
U.S. Appl. No. 18/122,456, filed Mar. 16, 2023.
U.S. Appl. No. 18/122,486, filed Mar. 16, 2023.
U.S. Appl. No. 18/122,504, filed Mar. 16, 2023.
U.S. Appl. No. 18/444,972, filed Feb. 19, 2024.
U.S. Appl. No. 18/447,025, filed Aug. 9, 2023.
U.S. Appl. No. 18/447,050, filed Aug. 9, 2023.
U.S. Appl. No. 18/447,064, filed Aug. 9, 2023.
U.S. Appl. No. 18/447,074, filed Aug. 9, 2023.
U.S. Appl. No. 18/447,086, filed Aug. 9, 2023.
U.S. Appl. No. 18/511,532, filed Nov. 16, 2023.
U.S. Appl. No. 18/632,533, filed Apr. 11, 2024.
U.S. Appl. No. 18/632,545, filed Apr. 11, 2024.
U.S. Appl. No. 18/632,557, filed Apr. 11, 2024.
U.S. Appl. No. 18/632,569, filed Apr. 11, 2024.
U.S. Appl. No. 18/635,275, filed Apr. 15, 2024.
U.S. Appl. No. 18/635,286, filed Apr. 15, 2024.
U.S. Appl. No. 18/635,292, filed Apr. 15, 2024.
U.S. Appl. No. 18/637,653, filed Apr. 17, 2024.
U.S. Appl. No. 18/637,655, filed Apr. 17, 2024.
U.S. Appl. No. 18/637,667, filed Apr. 17, 2024.
U.S. Appl. No. 18/639,079, filed Apr. 18, 2024.
U.S. Appl. No. 18/639,087, filed Apr. 18, 2024.
U.S. Appl. No. 18/639,094, filed Apr. 18, 2024.
U.S. Appl. No. 18/639,098, filed Apr. 18, 2024.
U.S. Appl. No. 18/640,222, filed Apr. 19, 2024.
U.S. Appl. No. 18/640,260, filed Apr. 19, 2024.
U.S. Appl. No. 18/640,285, filed Apr. 19, 2024.
U.S. Appl. No. 18/640,303, filed Apr. 19, 2024.
U.S. Appl. No. 18/652,930, filed May 2, 2024.
U.S. Appl. No. 18/652,956, filed May 2, 2024.
U.S. Appl. No. 18/652,959, filed May 2, 2024.
U.S. Appl. No. 18/652,962, filed May 2, 2024.
U.S. Appl. No. 18/654,336, filed May 3, 2024.
U.S. Appl. No. 61/656,244, filed Jun. 6, 2012.
U.S. Appl. No. 61/779,803, filed Mar. 13, 2013.
U.S. Appl. No. 61/914,470, filed Dec. 11, 2013.
U.S. Appl. No. 61/914,475, filed Dec. 11, 2013.
U.S. Appl. No. 62/000,192, filed May 19, 2014.
U.S. Appl. No. 62/162,881, filed May 18, 2015.
U.S. Appl. No. 62/401,403, filed Sep. 29, 2016.
U.S. Appl. No. 62/412,631, filed Oct. 25, 2016.
U.S. Appl. No. 62/425,814, filed Nov. 23, 2016.
U.S. Appl. No. 62/543,540, filed Aug. 10, 2017.
U.S. Appl. No. 62/615,538, filed Jan. 10, 2018.
U.S. Appl. No. 62/665,718, filed May 2, 2018.
U.S. Appl. No. 62/681,868, filed Jun. 7, 2018.
U.S. Appl. No. 62/727,605, filed Sep. 6, 2018.
U.S. Appl. No. 62/796,138, filed Jan. 24, 2019.
U.S. Appl. No. 62/851,716, filed May 23, 2019.
U.S. Appl. No. 62/870,821, filed Jul. 5, 2019.
U.S. Appl. No. 62/896,026, filed Sep. 5, 2019.
U.S. Appl. No. 63/003,955, filed Apr. 2, 2020.
U.S. Appl. No. 63/006,122, filed Apr. 7, 2020.
U.S. Appl. No. 63/114,136, filed Nov. 16, 2020.
U.S. Appl. No. 63/129,983, filed Dec. 23, 2020.
U.S. Appl. No. 63/158,708, filed Mar. 9, 2021.
U.S. Appl. No. 63/254,321, filed Oct. 11, 2021.
U.S. Appl. No. 63/317,199, filed Mar. 7, 2022.
U.S. Appl. No. 63/406,427, filed Sep. 14, 2022.
U.S. Appl. No. 63/432,496, filed Dec. 14, 2022.
U.S. Appl. No. 63/443,519, filed Feb. 6, 2023.
U.S. Appl. No. 63/470,259, filed Jun. 1, 2023.
"Compendium of Technical and Scientific Information for the Hemopump Temporary Cardiac Assist System" , Johnson & Johnson Interventional Systems , 1988 , pp. 1-15.
"Translation of decision of Board 4 (Nullity Board) of the German Federal Patent Court re German patent 10336902" , pronounced Nov. 15, 2016, and appendices to decision , 62 pages.

(56) References Cited

OTHER PUBLICATIONS

Achour , et al. , "Mechanical Left Ventricular Unloading Prior to Reperfusion Reduces Infarct Size in a Canine Infarction Model", Catheterization and Cardiovascular Interventions 64 , 2005 , pp. 182-192.
Agarwal , et al. , "Newer-generation ventricular assist devices" , Best Practice & Research Clinical Anaesthesiology , 2012 , pp. 117-130.
Alba , et al. , "The future is here: ventricular assist devices for the failing heart", Expert review of cardiovascular therapy , 2009 , pp. 1067-1077.
Bai , et al. , "A Split-Array, C-2C Switched-Capacitor Power Amplifier in 65 nm CMOS", IEEE Radio Frequency Integrated Circuits Symposium , 2017 , pp. 336-339.
Burnett , et al. , "Renal Interstitial Pressure and Sodium Excretion During Renal Vein Constriction" , American Physiological Society , 1980 , pp. F279-F282.
Butler , et al. , "The Hemopump—A New Cardiac Prothesis Device", Reprinted from IEEE Transactions on Biomedical Engineering, vol. 37, No. 2 , Feb. 1990 , pp. 192-195.
Cassidy , et al. , "The Conductance Volume Catheter Technique for Measurement of Left Ventricular Volume in Young Piglets", Pediatric Research , 1992 , pp. 85-90.
Chan , et al. , "Rapid manufacturing techniques in the development of an axial blood pump impeller", Proc. Instn Mech. Engrs vol. 217 Part H: J. Engineering in Medicine , 2003 , pp. 469-475.
Chang , et al. , "Leveraging Device-Arterial Coupling to Determine Cardiac and Vascular State", IEEE Transactions on Biomedical Engineering, vol. 66, No. 10 , Oct. 2019 , pp. 2800-2808.
Coxworth , "Artificial Vein Valve Could Replace Drugs for Treating Common Circulatory Problem", Published on Gizmag website (http://www.gizmag.com/artificial-venous-valve-cvi/21785/) , Mar. 9, 2012.
Damman , et al. , "Decreased Cardiac Output, Venous Congestion and the Association With Renal Impairment in Patients With Cardiac Dysfunction" , European Journal of Heart Failure , 2007 , pp. 872-878.
Damman , et al. , "Increased Central Venous Pressure Is Associated With Impaired Renal Function and Mortality in a Broad Spectrum of Patients With Cardiovascular Disease", Journal of American College of Cardiology , 2009 , pp. 582-588.
Dekker , et al. , "Efficacy of a New Intraaortic Propeller Pump vs the Intraaortic Balloon Pump", Chest, vol. 123, Issue 6 , Jun. 2003 , pp. 2089-2095.
Doty , et al. , "The Effect of Increased Renal Venous Pressure on Renal Function", The Journal of Trauma, , Dec. 1999 , pp. 1000-1003.
Felker , et al. , "Anemia as a Risk Factor and Therapeutic Target in Heart Failure" , Journal of the American College of Cardiology , 2004 , pp. 959-966.
Firth , et al. , "Raised Venous Pressure: A Direct Cause of Sodium Retention in Oedema?", The Lancet , May 7, 1988 , pp. 1033-1036.
Flameng , "Temporary Cardiac Assist with an Axial Pump System", Steinkopff Verlag Darmstadt , 1991 , 79 pages.
Forman , et al. , "Incidence, Predictors at Admission, and Impact of Worsening Renal Function Among Patients Hospitalized With Heart Failure", Journal of American College of Cardiology , 2004 , pp. 61-67.
Fraser , et al. , "The use of computational fluid dynamics in the development of ventricular assist devices", Medical engineering & physics , 2011 , pp. 263-280.
Frazier , et al. , "First Human Use of the Hemopump, a CatheterMounted Ventricular Assist Device", Ann Thorac Surg , 1990 , pp. 299-304.
Frazier , et al. , "Treatment of Cardiac Allograft Failure by use of an IntraAortic Axial Flow Pump", Journal of Heart Transplantation, St. Louis, vol. 9, No. 4 , pp. 408-414 , Jul. 1990.
Gomes , et al. , "Heterologous Valve Implantation in the Infra-Renal Vena Cava for Treatment of the Iliac Venous Valve Regurgitation Disease: Experimental Study" , Rev Bras Cir Cardiovasc , 2002 , pp. 367-369.
Gunther , et al. , "Experimentelle Radiologie", Life Sciences, Berichte Aus Der Rheinischwestfälischen Technischen Hochschule Aachen Ausgabe Feb. 2002.
Haddy , et al. , "Effect of Elevation of Intraluminal Pressure on Renal Vascular Resistance", Circulation Research Journal of the American Heart Association , 1956 , pp. 659-663.
Heywood , et al. , "High Prevalence of Renal Dysfunction and Its Impact on Outcome in 118,465 Patients Hospitalized With Acute Decompensated Heart Failure: A Report From the ADHERE Database", Journal of Cardiac Failure , 2007 , pp. 422-430.
Hillege , et al. , "Renal Function as a Predictor of Outcome in a Broad Spectrum of Patients With Heart Failure", Circulation Journal of the American Heart Association , 2006 , pp. 671-678.
Hillege , et al. , "Renal Function, Neurohormonal Activation, and Survival in Patients With Chronic Heart Failure", Circulation Journal of the American Heart Association , 2000 , pp. 203-210.
Hsu , et al. , "Review of recent patents on foldable ventricular assist devices", Recent Patents on Biomedical Engineering , 2012 , pp. 208-222.
Ikari , "The Physics of Guiding Catheter; The IKARI Guiding Catheter in TRI", available at httu:i /www.docstoccom/docs/148136553/The-[KARI-catheter---anovel-guide-for-TRI--.
Kafagy , et al. , "Design of axial blood pumps for patients with dysfunctional fontan physiology: computational studies and performance testing", Artificial organs , 2015 , pp. 34-42.
Kang , et al. , "Fluid dynamics aspects of miniaturized axial-flow blood pump", Bio-medical materials and engineering , 2014 , pp. 723-729.
Keller , et al. , "Dynamic Modulation of Device-Arterial Coupling to Determine Cardiac Output and Vascular Resistance", Annals of Biomedical Engineering, vol. 48, No. 9 , Sep. 2020 , pp. 2333-2342.
Koochaki , et al. , "A new design and computational fluid dynamics study of an implantable axial blood pump", Australasian Physical & Engineering Sciences in Medicine , 2013 , pp. 417-422.
Lauten , et al. , "Heterotopic Transcatheter Tricuspid Valve Implantation: First-In-Man Application of a Novel Approach to Tricuspid Regurgitation", European Heart Journal , Feb. 15, 2011 , pp. 1207-1213.
Ledoux , et al. , "Left Ventricular Unloading With Intra-aortic Counter Pulsation Prior to Reperfusion Reduces Myocardial Release of Endothelin-1 and Decreases Infarction Size in a Porcine Ischemia-Reperfusion Model", Catheterization and Cardiovascular Interventions 72 , 2008 , pp. 513-521.
Mcalister , et al. , "Renal Insufficiency and Heart Failure: Prognostic and Therapeutic Implications From a Prospective Cohort Study", Circulation Journal of the American Heart Association , 2004 , pp. 1004-1009.
Merhige , et al. , "Effect of the Hemopump Left Ventricular Assist Device on Regional Myocardial Perfusion and Function", Reduction of Ischemia during Coronary Occlusion, Johnson & Johnson Interventional Systems Supplement 3, Circulation vol. 80, No. 5 , Nov. 1989 , pp. III-159-III-166.
Meyns , et al. , "The Heart-Hemopump Interaction: A Study of Hemopump Flow as a Function of Cardiac Activity", Artificial Organs , 1996 , pp. 641-649.
Mullens , et al. , "Elevated Intra-Abdominal Pressure in Acute Decompensated Heart Failure. A Potential Contributor to Worsening Renal Function", Journal of the American College of Cardiology , 2008 , pp. 300-306.
Mullens , et al. , "Importance of Venous Congestion for Worsening of Renal Function in Advanced Decompensated Heart Failure", Journal of American College of Cardiology , 2009 , pp. 589-596.
Mullens , et al. , "Prompt Reduction in Intra-Abdominal Pressure Following Large-Volume Mechanical Fluid Removal Improves Renal Insufficiency in Refractory Decompensated Heart Failure", Journal of Cardiac Failure , 2008 , pp. 508-514.
Notarius , et al. , "Central Venous Pressure During Exercise: Role of Muscle Pump", Canadian Journal of Physiology and Pharmacology , 1996 , pp. 647-651.
Park , et al. , "Nutcracker Syndrome: Intravascular Stenting Approach", Nephrol Dial Transplant , 2000 , pp. 99-101.
Reul , et al. , "Blood pumps for circulatory support", Perfusion-Sevenoaks , 2000 , pp. 295-312.

(56) References Cited

OTHER PUBLICATIONS

Reul , et al. , "Rotary blood pumps in circulatory assist", Perfusion , May 1995 , pp. 153-158.
Rodefeld , "Cavopulmonary assist for the univentricular Fontan circulation: von Karman viscous impeller pump", The Journal of Thoracic and Cardiovascular Surgery , 2010 , pp. 529-536.
Roundtree , et al. , "The Hemopump Cardiac Assist System: Nursing Care of the Patient", Reprinted from Critical Care Nurse , Apr. 1991.
Schmitz-Rode , et al. , "An Expandable Percutaneous Catheter Pump for Left Ventricular Support", Journal of the American College of Cardiology, vol. 45, No. 11 , 2005 , pp. 1856-1861.
Schmitz-Rode , et al. , "Axial flow catheter pump for circulatory support", Biomed Tech (Berl) , 2002 , pp. 142-143.
Scholz , et al. , "Mechanical left Ventricular Unloading During High Risk Coronary Angioplasty: First Use of a New Percutaneous Transvalvular Left Ventricular Assist Device", Catheterization and Cardiovascular Diagnosis 31 , 1994 , pp. 61-69.
Semple , et al. , "Effect of Increased Renal Venous Pressure on Circulatory "Autoregulation" of Isolated Dog Kidneys", Circulation Research Journal of the American Heart Association , 1959 , pp. 643-648.
Sianos , et al. , "The Recover® LP 2.5 catheter-mounted left ventricular assist device", EuroIntervention , 2006 , pp. 116-119.
Siess , et al. , "Concept, realization, and first in vitro testing of an intraarterial microaxial blood pump", Artificial Organs , 1995 , pp. 644-652.
Siess , et al. , "Hemodynamic system analysis of intraarterial microaxial pumps in vitro and in vivo", Artificial Organs , Jun. 1996 , pp. 650-661.
Siess , "PhD Chapter 3—English translation" https://www.shaker.eu/en/content/catalogue/index.asp?lang=en&ID=8&ISBN=978-3-8265-6150-4&search=yes.
Siess , "System Analysis and Development of Intravascular Rotation Pumps for Cardiac Assist", Helmholtz-Institute—Chapter 3 , Jun. 1998 , 17 pages.
Smalling , et al. , "Improved Regional Myocardial Blood Flow, Left Ventricular Unloading, and Infarct Salvage Using an Axial-Flow, Transvalvular Left Ventricular Assist Device", A Comparison With Intra-Aortic Balloon Counterpulsation and Reperfusion Alone in a Canine Infarction Model, Presented in part at the American College of Cardiology 38th Annual Scientific Session , Mar. 1990 , pp. 1152-1160.
Smalling , et al. , "The Hemopump: A transvalvular, axial flow, left ventricular assist device", Coronary Artery Disease, Circulatory support devices in clinical cardiology, vol. 2 No. 6 , pp. 666-671 , Aug. 1991.
Smalling , et al. , "Transvalvular Left Ventricular Assistance in Cardiogenic Shock Secondary to Acute Myocardial Infarction", Evidence for Recovery From Near Fatal Myocardial Stunning, JACC vol. 23, No. 3 , pp. 637-644 , Mar. 1, 1994.
Song , et al. , "Axial flow blood pumps", ASAIO journal , 2003 , pp. 355-364.
Tamareille , et al. , "Left ventricular unloading before reperfusion reduces endothelin-1 release and calcium overload in porcine myocardial infarction", Cardiopulmonary Support and Physiology, The Journal of Thoracic and Cardiovascular Surgery, vol. 136, No. 2 , 2008 , pp. 343-351.
Tang , et al. , "Anemia in Chronic Heart Failure: Prevalence, Etiology, Clinical Correlates, and Treatment Options", Circulation Journal of the American Heart Association , 2006 , pp. 2454-2461.
Throckmorton , et al. , "Design of a protective cage for an intra vascular axial flow blood pump to mechanically assist the failing Fontan", Artificial organs , 2009 , pp. 611-621.
Throckmorton , et al. , "Mechanical Cavopulmonary Assist for the Univentricular Fontan Circulation Using a Novel Folding Propeller Blood Pump", ASAIO Journal , 2007 , pp. 734-741.
Thunberg , et al. , "Ventricular assist devices today and tomorrow", Journal of cardiothoracic and vascular anesthesia , 2010 , pp. 656-680.
Timms , "A review of clinical ventricular assist devices", Medical engineering & physics , 2011, pp. 1041-1047.
Triep , et al. , "Computational Fluid Dynamics and Digital Particle Image Velocimetry Study of the Flow Through an Optimized Micro-axial Blood Pump", Artificial Organs , May 2006 , pp. 384-391.
Uthoff , et al. , "Central venous pressure at emergency room presentation predicts cardiac rehospitalization in patients with decompensated heart failure", European Journal of Heart Failure , 2010 , pp. 469-476.
Van Mieghem , et al. , "Design and Principle of Operation of the HeartMate PHPTM (Percutaneous Heart Pump)" , EuroIntervention , 2016.
Vercaemst , et al. , "Impella: A Miniaturized Cardiac Support System in an Era of Minimal Invasive Cardiac Surgery", Presented at the 39th International Conference of the American Society of Extra-Corporeal Technology , Mar. 22-25, 2001.
Wampler , "Newspaper Articles", Captain Hemo , 1988 , 6 pages.
Wampler , "Newsweek", Captain Hemo , May 16, 1988 , 3 pages.
Wampler , "The first co-axial flow pump for human use: the Hemopump", Flameng W. (eds) Temporary Cardiac Assist with an Axial Pump System , 1991.
Wampler , "THI Today", Captain Hemo , Summer 1988 , 2 pages.
Wampler , "Time Magazine", Captain Hemo , May 1988 , 2 pages.
Wampler , et al. , "Treatment of Cardiogenic Shock With the Hemopump Left Ventricular Assist Device", Annual of Thoracic Surgery, vol. 52 , pp. 560-513 , 1991.
Wampler , "U.S. News & World Report", Captain Hemo , pp. 1-2 , May 16, 1988.
Wencker , "Acute Cardio-Renal Syndrome: Progression From Congestive Heart Failure to Congestive Kidney Failure", Current Heart Failure Reports , 2007 , pp. 134-138.
Winton , "The Control of Glomerular Pressure by Vascular Changes Within the Mammalian Kidney, Demonstrated by the Actions of Adrenaline", Journal of Physiology , Nov. 1931 pp. 151-162.
Winton , "The Influence of Venous Pressure on the Isolated Mammalian Kidney", Journal of Physiology , Jun. 6, 1931 , pp. 49-61.
Wood , "The Mechanism of the Increased Venous Pressure With Exercise in Congestive Heart Failure", Journal of Clinical Investigation , 1962 , pp. 2020-2024.
Wu , et al. , "Design and simulation of axial flow maglev blood pump", International Journal of Information Engineering and Electronic Business , 2011 , p. 42.
Yancy , et al. , "Clinical Presentation, Management, and In-Hospital Outcomes of Patients Admitted With Acute Decompensated Heart Failure With Preserved Systolic Function. A Report From the Acute Decompensated Heart Failure National Registry (ADHERE) Database", Journal of the American College of Cardiology , 2006 , pp. 76-84.
Corrected Notice of Allowance for U.S. Appl. No. 16/952,327 mailed Sep. 20, 2024.
Corrected Notice of Allowance for U.S. Appl. No. 17/069,570 mailed Jul. 16, 2024.
Corrected Notice of Allowance for U.S. Appl. No. 17/528,807 mailed Sep. 19, 2024.
Corrected Notice of Allowance for U.S. Appl. No. 17/857,402 mailed Nov. 7, 2024.
Corrected Notice of Allowance for U.S. Appl. No. 17/857,402 mailed Oct. 30, 2024.
Examination Report for European Application No. 21158903.1 mailed Jul. 9, 2024.
Extended Search Report for European Application No. 24170573.0 mailed Jul. 29, 2024.
Final Office Action for U.S. Appl. No. 17/078,472 mailed Aug. 9, 2024.
Hearing Notice for Indian Application No. 202147033522 mailed Jul. 24, 2024.
Issue Notification for U.S. Appl. No. 16/952,327 mailed Oct. 9, 2024.
Issue Notification for U.S. Appl. No. 17/574,701 mailed Aug. 28, 2024.
Issue Notification for U.S. Appl. No. 17/528,807 mailed Oct. 9, 2024.

(56) References Cited

OTHER PUBLICATIONS

Non-Final Office Action for U.S. Appl. No. 17/528,015 mailed Oct. 21, 2024.
Non-Final Office Action for U.S. Appl. No. 17/532,318 mailed Jul. 18, 2024.
Non-Final Office Action for U.S. Appl. No. 17/677,571 mailed Aug. 15, 2024.
Non-Final Office Action for U.S. Appl. No. 17/678,812 mailed Sep. 26, 2024.
Non-Final Office Action for U.S. Appl. No. 17/682,073 mailed Aug. 29, 2024.
Non-Final Office Action for U.S. Appl. No. 17/682,104 mailed Sep. 30, 2024.
Non-Final Office Action for U.S. Appl. No. 18/511,532 mailed Aug. 27, 2024.
Notice of Allowance for U.S. Appl. No. 16/952,327 mailed Aug. 6, 2024.
Notice of Allowance for U.S. Appl. No. 17/070,670 mailed Sep. 11, 2024.
Notice of Allowance for U.S. Appl. No. 17/528,807 mailed Sep. 9, 2024.
Notice of Allowance for U.S. Appl. No. 17/857,402 mailed Oct. 8, 2024.
Office Action for Japanese Application No. 2023-156391 mailed Jun. 3, 2024.
Office Action for Japanese Application No. 2023-191120 mailed Oct. 1, 2024.
Restriction Requirement for U.S. Appl. No. 17/722,752 mailed Sep. 12, 2024.
Restriction Requirement for U.S. Appl. No. 17/723,150 mailed Sep. 11, 2024.
Restriction Requirement for U.S. Appl. No. 17/723,656 mailed Sep. 12, 2024.
U.S. Appl. No. 18/882,984, filed Sep. 12, 2024.
U.S. Appl. No. 18/889,744, filed Sep. 19, 2024.
U.S. Appl. No. 18/933,729, filed Oct. 31, 2024.
U.S. Appl. No. 18/933,745, filed Oct. 31, 2024.
U.S. Appl. No. 18/933,749, filed Oct. 31, 2024.
U.S. Appl. No. 18/933,759, filed Oct. 31, 2024.
"Peripheral Interventions 2015 Product Catalog", Boston Scientific, 2015, 7 pages.
Alsafarr , et al., "Hydrodynamic Effects on Flow Through Screens at Intakes", Water Research vol. 8, Issue 9, Sep. 1974, pp. 617-622.
Brückler , et al., "Flow Design and Optimization of a Percutaneously Implantable Miniature Blood Pump", Medical technology in cardiology, 2002, 11 pages.
Fox , et al., "Introduction to Fluid Mechanics", Sixth Edition, pp. 341-343.
Kapur , et al., "Mechanical Left Ventricular Unloading to Reduce Infarct Size During Acute Myocardial Infarction: Insight from Preclinical and Clinical Studies", Journal of Cardiovascular Translational Research, Apr. 23, 2019, pp. 1-8.
Kaufman , "Invasive Vascular Diagnosis", Radiology Key Fastest Radiology Insight Engine, Chapter 3, Dec. 23, 2015, 12 pages.
Schmitz-Rode , "Percutaneously implantable, self-expanding left heart support pump", Clinic for Radiological Diagnostics, 2001, 19 Pages.
Siess , et al., "Basic Design Criteria for Rotary Blood Pumps", Rotary Blood Pumps, 2000, pp. 69-83.
Corrected Notice of Allowance for U.S. Appl. No. 17/528,015 mailed Apr. 11, 2025.
Corrected Notice of Allowance for U.S. Appl. No. 17/528,015 mailed May 13, 2025.
Corrected Notice of Allowance for U.S. Appl. No. 17/609,589 mailed Feb. 24, 2026.
Corrected Notice of Allowance for U.S. Appl. No. 17/678,122 mailed May 27, 2025.
Corrected Notice of Allowance for U.S. Appl. No. 17/722,752 mailed Jul. 25, 2025.
Corrected Notice of Allowance for U.S. Appl. No. 17/723,150 mailed Apr. 24, 2025.
Corrected Notice of Allowance for U.S. Appl. No. 17/907,618 mailed Apr. 27, 2026.
Corrected Notice of Allowance for U.S. Appl. No. 18/122,456 mailed Feb. 19, 2026.
Corrected Notice of Allowance for U.S. Appl. No. 18/122,486 mailed Dec. 17, 2025.
Corrected Notice of Allowance for U.S. Appl. No. 18/511,532 mailed May 5, 2026.
Corrected Notice of Allowance for U.S. Appl. No. 18/933,729 mailed Jul. 2, 2025.
Corrected Notice of Allowance for U.S. Appl. No. 18/933,729 mailed Jul. 23, 2025.
Examination Report for Australian Application No. 2021253815 mailed Apr. 15, 2026.
Examination Report for Australian Application No. 2021253815 mailed Dec. 19, 2025.
Examination Report for Australian Application No. 2024203274 mailed May 1, 2025.
Examination Report for Australian Application No. 2025200291 mailed Sep. 16, 2025.
Examination Report for Indian Application No. 202247058135 mailed Jan. 27, 2026.
Examination Report for Indian Application No. 202417030022 mailed May 4, 2026.
Examination Report for Indian Application No. 202517007844 mailed Jul. 10, 2026.
Extended Search Report for European Application No. 24200871.2 mailed Jan. 30, 2025.
Extended Search Report for European Application No. 24200875.3 mailed Jan. 13, 2025.
Extended Search Report for European Application No. 24206716.3 mailed Nov. 21, 2024.
Extended Search Report for European Application No. 24209593.3 mailed Dec. 4, 2024.
Extended Search Report for European Application No. 24209594.1 mailed Dec. 4, 2024.
Extended Search Report for European Application No. 24211523.6 mailed Feb. 7, 2025.
Extended Search Report for European Application No. 24211525.1 mailed Feb. 20, 2025.
Extended Search Report for European Application No. 25151821.3 mailed Apr. 14, 2025.
Extended Search Report for European Application No. 25163036.4 mailed Jul. 25, 2025.
Extended Search Report for European Application No. 25163043.0 mailed Jul. 28, 2025.
Extended Search Report for European Application No. 25204084.5 mailed Feb. 2, 2026.
Extended Search Report for European Application No. 26152673.5 mailed Jun. 24, 2026.
Extended Search Report for European Application No. 26153273.3 mailed Jun. 24, 2026.
Final Office Action for U.S. Appl. No. 17/078,472 mailed Mar. 12, 2025.
Final Office Action for U.S. Appl. No. 17/176,344 mailed Oct. 7, 2025.
Final Office Action for U.S. Appl. No. 17/677,571 mailed Apr. 15, 2026.
Final Office Action for U.S. Appl. No. 17/678,812 mailed May 28, 2025.
Final Office Action for U.S. Appl. No. 17/682,073 mailed Feb. 23, 2026.
Final Office Action for U.S. Appl. No. 17/723,656 mailed Apr. 8, 2025.
Final Office Action for U.S. Appl. No. 17/723,656 mailed Jun. 2, 2026.
Final Office Action for U.S. Appl. No. 17/907,618 mailed Nov. 24, 2025.
Final Office Action for U.S. Appl. No. 18/001,680 mailed Dec. 23, 2025.

(56) References Cited

OTHER PUBLICATIONS

Final Office Action for U.S. Appl. No. 18/121,995 mailed Dec. 19, 2025.
Final Office Action for U.S. Appl. No. 18/122,504 mailed May 5, 2026.
Final Office Action for U.S. Appl. No. 18/122,504 mailed Oct. 23, 2025.
Final Office Action for U.S. Appl. No. 18/511,532 mailed Apr. 11, 2025.
Final Office Action for U.S. Appl. No. 18/632,533 mailed Jun. 15, 2026.
Final Office Action for U.S. Appl. No. 18/632,557 mailed Jul. 13, 2026.
Final Office Action for U.S. Appl. No. 18/640,260 mailed Jul. 30, 2026.
Final Office Action for U.S. Appl. No. 18/652,959 mailed Jul. 1, 2026.
International Search Report and Written Opinion from International Application No. PCT/IB2024/063109 mailed Jun. 2, 2025.
International Search Report and Written Opinion from International Application No. PCT/IB2024/063110 mailed Jun. 2, 2025.
International Search Report and Written Opinion from International Application No. PCT/IB2024/063113 mailed Jun. 11, 2025.
International Search Report and Written Opinion from International Application No. PCT/IB2024/063115 mailed Jun. 19, 2025.
International Search Report and Written Opinion from International Application No. PCT/IB2025/056384 mailed Dec. 16, 2025.
International Search Report and Written Opinion from International Application No. PCT/IB2025/056385 mailed Jan. 16, 2026.
International Search Report and Written Opinion from International Application No. PCT/IB2025/059116 mailed Jan. 2, 2026.
Invitation to Pay Additional Fees for International Application No. PCT/IB2024/063113 mailed Apr. 17, 2025.
Invitation to Pay Additional Fees for International Application No. PCT/IB2024/063115 mailed Apr. 15, 2025.
Invitation to Pay Additional Fees for International Application No. PCT/IB2025/056384 mailed Oct. 9, 2025.
Invitation to Pay Additional Fees for International Application No. PCT/IB2025/056385 mailed Oct. 1, 2025.
Invitation to Pay Additional Fees for International Application No. PCT/IB2025/059116 mailed Nov. 4, 2025.
Invitation to Pay Additional Fees for International Application No. PCT/IB2026/053511 mailed Jul. 8, 2026.
Invitation to Pay Additional Fees for International Application No. PCT/IB2026/053512 mailed Jul. 17, 2026.
Issue Notification for U.S. Appl. No. 17/070,670 mailed Jan. 8, 2025.
Issue Notification for U.S. Appl. No. 17/528,015 mailed Jun. 18, 2025.
Issue Notification for U.S. Appl. No. 17/532,318 mailed Oct. 1, 2025.
Issue Notification for U.S. Appl. No. 17/609,589 mailed May 6, 2026.
Issue Notification for U.S. Appl. No. 17/678,122 mailed Jun. 4, 2025.
Issue Notification for U.S. Appl. No. 17/722,752 mailed Oct. 15, 2025.
Issue Notification for U.S. Appl. No. 17/723,150 mailed Oct. 1, 2025.
Issue Notification for U.S. Appl. No. 17/857,402 mailed Dec. 18, 2024.
Issue Notification for U.S. Appl. No. 17/907,618 mailed Jul. 22, 2026.
Issue Notification for U.S. Appl. No. 18/122,456 mailed Feb. 25, 2026.
Issue Notification for U.S. Appl. No. 18/122,486 mailed Jan. 28, 2026.
Issue Notification for U.S. Appl. No. 18/511,532 mailed May 20, 2026.
Issue Notification for U.S. Appl. No. 18/933,729 mailed Jan. 28, 2026.
Liu, et al., "Crystallinity and Oxygen Transport Properties of PET Bottle Walls" Journal of Applied Polymer Science, vol. 94, pp. 671-677, 2004.
Non-Final Office Action for U.S. Appl. No. 17/078,472 mailed Aug. 12, 2025.
Non-Final Office Action for U.S. Appl. No. 17/078,472 mailed Nov. 19, 2024.
Non-Final Office Action for U.S. Appl. No. 17/176,344 mailed Feb. 20, 2025.
Non-Final Office Action for U.S. Appl. No. 17/609,589 mailed Jan. 30, 2025.
Non-Final Office Action for U.S. Appl. No. 17/609,589 mailed Sep. 5, 2025.
Non-Final Office Action for U.S. Appl. No. 17/677,571 mailed Aug. 20, 2025.
Non-Final Office Action for U.S. Appl. No. 17/677,571 mailed Feb. 20, 2025.
Non-Final Office Action for U.S. Appl. No. 17/678,122 mailed Dec. 5, 2024.
Non-Final Office Action for U.S. Appl. No. 17/678,812 mailed Dec. 3, 2025.
Non-Final Office Action for U.S. Appl. No. 17/682,073 mailed May 28, 2025.
Non-Final Office Action for U.S. Appl. No. 17/682,104 mailed Jan. 16, 2026.
Non-Final Office Action for U.S. Appl. No. 17/682,104 mailed May 28, 2025.
Non-Final Office Action for U.S. Appl. No. 17/722,752 mailed Mar. 17, 2025.
Non-Final Office Action for U.S. Appl. No. 17/723,150 mailed Dec. 19, 2024.
Non-Final Office Action for U.S. Appl. No. 17/723,656 mailed Dec. 5, 2024.
Non-Final Office Action for U.S. Appl. No. 17/723,656 mailed Nov. 3, 2025.
Non-Final Office Action for U.S. Appl. No. 17/907,618 mailed May 2, 2025.
Non-Final Office Action for U.S. Appl. No. 18/001,680 mailed Jun. 20, 2025.
Non-Final Office Action for U.S. Appl. No. 18/121,995 mailed Mar. 27, 2025.
Non-Final Office Action for U.S. Appl. No. 18/122,504 mailed Mar. 5, 2025.
Non-Final Office Action for U.S. Appl. No. 18/444,972 mailed Dec. 9, 2025.
Non-Final Office Action for U.S. Appl. No. 18/444,972 mailed Jun. 11, 2026.
Non-Final Office Action for U.S. Appl. No. 18/447,025 mailed Nov. 5, 2025.
Non-Final Office Action for U.S. Appl. No. 18/511,532 mailed Aug. 18, 2025.
Non-Final Office Action for U.S. Appl. No. 18/632,533 mailed Jan. 30, 2026.
Non-Final Office Action for U.S. Appl. No. 18/632,545 mailed Jan. 13, 2026.
Non-Final Office Action for U.S. Appl. No. 18/632,557 mailed Feb. 24, 2026.
Non-Final Office Action for U.S. Appl. No. 18/635,275 mailed Jul. 28, 2026.
Non-Final Office Action for U.S. Appl. No. 18/635,292 mailed Jul. 23, 2026.
Non-Final Office Action for U.S. Appl. No. 18/637,667 mailed Feb. 17, 2026.
Non-Final Office Action for U.S. Appl. No. 18/637,667 mailed Jul. 14, 2026.
Non-Final Office Action for U.S. Appl. No. 18/639,079 mailed Apr. 7, 2026.
Non-Final Office Action for U.S. Appl. No. 18/639,087 mailed Apr. 7, 2026.
Non-Final Office Action for U.S. Appl. No. 18/639,098 mailed Mar. 6, 2026.

(56) References Cited

OTHER PUBLICATIONS

Non-Final Office Action for U.S. Appl. No. 18/640,222 mailed Apr. 15, 2026.
Non-Final Office Action for U.S. Appl. No. 18/640,260 mailed Feb. 17, 2026.
Non-Final Office Action for U.S. Appl. No. 18/640,285 mailed Jan. 26, 2026.
Non-Final Office Action for U.S. Appl. No. 18/640,303 mailed Apr. 1, 2026.
Non-Final Office Action for U.S. Appl. No. 18/652,930 mailed Dec. 31, 2025.
Non-Final Office Action for U.S. Appl. No. 18/652,956 mailed Apr. 10, 2026.
Non-Final Office Action for U.S. Appl. No. 18/652,959 mailed Oct. 1, 2025.
Non-Final Office Action for U.S. Appl. No. 18/652,962 mailed Apr. 17, 2026.
Non-Final Office Action for U.S. Appl. No. 18/654,336 mailed Apr. 30, 2026.
Non-Final Office Action for U.S. Appl. No. 18/882,984 mailed Apr. 24, 2026.
Non-Final Office Action for U.S. Appl. No. 18/933,745 mailed Jun. 16, 2026.
Non-Final Office Action for U.S. Appl. No. 18/933,759 mailed Jun. 23, 2026.
Non-Final Office Action for U.S. Appl. No. 19/011,892 mailed Jul. 7, 2026.
Non-Final Office Action for U.S. Appl. No. 19/013,744 mailed Jun. 15, 2026.
Non-Final Office Action for U.S. Appl. No. 19/014,344 mailed Jul. 21, 2026.
Non-Final Office Action for U.S. Appl. No. 19/576,211 mailed Jun. 25, 2026.
Non-Final Office Action for U.S. Appl. No. 19/631,329 mailed Jul. 1, 2026.
Non-Final Office Action for U.S. Appl. No. 19/631,338 mailed Jun. 25, 2026.
Non-Final Office Action for U.S. Appl. No. 19/636,115 mailed Jun. 17, 2026.
Notice of Allowance for U.S. Appl. No. 17/078,472 mailed Apr. 22, 2026.
Notice of Allowance for U.S. Appl. No. 17/078,472 mailed Dec. 17, 2025.
Notice of Allowance for U.S. Appl. No. 17/528,015 mailed Mar. 25, 2025.
Notice of Allowance for U.S. Appl. No. 17/532,318 mailed Feb. 25, 2025.
Notice of Allowance for U.S. Appl. No. 17/532,318 mailed Jun. 24, 2025.
Notice of Allowance for U.S. Appl. No. 17/609,589 mailed Feb. 4, 2026.
Notice of Allowance for U.S. Appl. No. 17/678,122 mailed Apr. 30, 2025.
Notice of Allowance for U.S. Appl. No. 17/678,812 mailed Apr. 21, 2026.
Notice of Allowance for U.S. Appl. No. 17/682,073 mailed Jul. 29, 2026.
Notice of Allowance for U.S. Appl. No. 17/722,752 mailed Jul. 7, 2025.
Notice of Allowance for U.S. Appl. No. 17/723,150 mailed Apr. 7, 2025.
Notice of Allowance for U.S. Appl. No. 17/723,150 mailed Jun. 17, 2025.
Notice of Allowance for U.S. Appl. No. 17/907,618 mailed Apr. 9, 2026.
Notice of Allowance for U.S. Appl. No. 18/122,456 mailed Aug. 14, 2025.
Notice of Allowance for U.S. Appl. No. 18/122,456 mailed Jan. 12, 2026.
Notice of Allowance for U.S. Appl. No. 18/122,486 mailed Dec. 9, 2025.
Notice of Allowance for U.S. Appl. No. 18/511,532 mailed Apr. 1, 2026.
Notice of Allowance for U.S. Appl. No. 18/632,545 mailed May 8, 2026.
Notice of Allowance for U.S. Appl. No. 18/639,094 mailed Jul. 28, 2026.
Notice of Allowance for U.S. Appl. No. 18/933,729 mailed Jul. 1, 2025.
Notice of Allowance for U.S. Appl. No. 18/933,729 mailed Nov. 18, 2025.
Notice of Allowance for U.S. Appl. No. 18/639,087 mailed Jul. 28, 2026.
Office Action for Canadian Application No. 3,246,015 mailed Apr. 1, 2026.
Office Action for Chinese Application No. 202180006817.8 mailed Jun. 13, 2025.
Office Action for Chinese Application No. 202210520564.2 mailed May 23, 2025.
Office Action for Chinese Application No. 202210540435.X mailed May 22, 2025.
Office Action for Chinese Application No. 202210580274.7 mailed May 22, 2025.
Office Action for Chinese Application No. 202210583463.X mailed Jun. 13, 2025.
Office Action for Chinese Application No. 202210583463.X mailed Nov. 17, 2025.
Office Action for Chinese Application No. 202210587585.6 mailed Jun. 13, 2025.
Office Action for Chinese Application No. 202210587598.3 mailed Jun. 6, 2025.
Office Action for Chinese Application No. 202210791551.9 mailed May 16, 2025.
Office Action for Chinese Application No. 202210802982.0 mailed May 16, 2025.
Office Action for Chinese Application No. 202210802982.0 mailed Oct. 24, 2025.
Office Action for Chinese Application No. 202210847103.6 mailed May 16, 2025.
Office Action for Chinese Application No. 202280006309.4 mailed Dec. 4, 2025.
Office Action for Chinese Application No. 202280015894.4 mailed Aug. 1, 2025.
Office Action for Chinese Application No. 202310541980.5 mailed Apr. 28, 2026.
Office Action for Chinese Application No. 202310541980.5 mailed Jun. 16, 2025.
Office Action for Chinese Application No. 202310542349.7 mailed Jun. 4, 2025.
Office Action for Chinese Application No. 202310542349.7 mailed Mar. 28, 2026.
Office Action for Chinese Application No. 202310542349.7 mailed Nov. 28, 2025.
Office Action for Chinese Application No. 202311574718.7 mailed Feb. 11, 2026.
Office Action for Chinese Application No. 202311574730.8 mailed Apr. 2, 2026.
Office Action for Chinese Application No. 202311574758.1 mailed Jan. 28, 2026.
Office Action for Japanese Application No. 2022-559757 mailed Dec. 23, 2024.
Office Action for Japanese Application No. 2023-191120 mailed Mar. 17, 2025.
Office Action for Japanese Application No. 2023-547155 mailed Jan. 30, 2026.
Office Action for Japanese Application No. 2024-066507 mailed Feb. 19, 2026.
Office Action for Japanese Application No. 2024-066507 mailed Jun. 11, 2025.
Office Action for Japanese Application No. 2024-196041 mailed Feb. 18, 2026.

(56) References Cited

OTHER PUBLICATIONS

Office Action for Japanese Application No. 2024-519263 mailed Jun. 23, 2026.
Office Action for Japanese Application No. 2025-061899 mailed May 27, 2026.
Restriction Requirement for U.S. Appl. No. 17/907,618 mailed Feb. 13, 2025.
Restriction Requirement for U.S. Appl. No. 18/001,680 mailed Mar. 28, 2025.
Restriction Requirement for U.S. Appl. No. 18/122,486 mailed Apr. 14, 2025.
Restriction Requirement for U.S. Appl. No. 18/635,275 mailed Mar. 27, 2026.
Restriction Requirement for U.S. Appl. No. 18/635,286 mailed Jan. 28, 2026.
Restriction Requirement for U.S. Appl. No. 18/635,292 mailed Jan. 15, 2026.
Restriction Requirement for U.S. Appl. No. 18/637,653 mailed Mar. 4, 2026.
Restriction Requirement for U.S. Appl. No. 18/639,094 mailed Mar. 9, 2026.
Restriction Requirement for U.S. Appl. No. 18/889,744 mailed May 19, 2026.
Restriction Requirement for U.S. Appl. No. 18/947,762 mailed Apr. 27, 2026.
Restriction Requirement for U.S. Appl. No. 18/949,258 mailed Jun. 12, 2026.
Suriano, et al., "Styrene-Free Liquid Resins for Composite Reformulation", Systemic Circular Economy Solutions for Fiber Reinforced Composites, Digital Innovations in Architecture, Engineering and Construction, pp. 99-123, 2022.
U.S. Appl. No. 18/947,762, filed Nov. 14, 2024.
U.S. Appl. No. 18/949,258, filed Nov. 15, 2024.
U.S. Appl. No. 18/955,121, filed Nov. 21, 2024.
U.S. Appl. No. 18/958,181, filed Nov. 25, 2024.
U.S. Appl. No. 18/958,189, filed Nov. 25, 2024.
U.S. Appl. No. 18/958,196, filed Nov. 25, 2024.
U.S. Appl. No. 18/958,200, filed Nov. 25, 2024.
U.S. Appl. No. 19/011,892, filed Jan. 7, 2025.
U.S. Appl. No. 19/013,727, filed Jan. 8, 2025.
U.S. Appl. No. 19/013,744, filed Jan. 8, 2025.
U.S. Appl. No. 19/014,336, filed Jan. 9, 2025.
U.S. Appl. No. 19/014,344, filed Jan. 9, 2025.
U.S. Appl. No. 19/459,719, filed Jan. 26, 2026.
U.S. Appl. No. 19/460,541, filed Jan. 27, 2026.
U.S. Appl. No. 19/463,581, filed Jan. 29, 2026.
U.S. Appl. No. 19/466,779, filed Feb. 2, 2026.
U.S. Appl. No. 19/550,456, filed Feb. 26, 2026.
U.S. Appl. No. 19/550,462, filed Feb. 26, 2026.
U.S. Appl. No. 19/565,891, filed Mar. 13, 2026.
U.S. Appl. No. 19/573,404, filed Mar. 20, 2026.
U.S. Appl. No. 19/576,211, filed Mar. 24, 2026.
U.S. Appl. No. 19/631,329, filed Mar. 27, 2026.
U.S. Appl. No. 19/631,338, filed Mar. 27, 2026.
U.S. Appl. No. 19/636,115, filed Apr. 1, 2026.
U.S. Appl. No. 19/636,154, filed Apr. 1, 2026.
U.S. Appl. No. 63/566,681, filed Mar. 18, 2024.
U.S. Appl. No. 63/615,377, filed Dec. 28, 2023.
U.S. Appl. No. 63/692,734, filed Sep. 10, 2024.

* cited by examiner

VENTRICULAR ASSIST DEVICE

CROSS-REFERENCES TO RELATED APPLICATIONS

The present application is a continuation of U.S. application Ser. No. 17/574,701 to Tuval (published as US 2022/0134083), entitled "Ventricular assist device," filed Jan. 13, 2022, which is a continuation of U.S. application Ser. No. 16/277,411 to Tuval (issued as U.S. Pat. No. 11,260,212), entitled "Ventricular assist device," filed Feb. 15, 2019, which is a continuation of International Application No. PCT/IL2017/051158 to Tuval (published as WO 18/078615), entitled "Ventricular assist device," filed Oct. 23, 2017, which claims priority from:

U.S. Provisional Patent App. No. 62/412,631 to Tuval, entitled "Ventricular assist device," filed Oct. 25, 2016; and U.S. Provisional Patent App. No. 62/543,540 to Tuval, entitled "Ventricular assist device," filed Aug. 10, 2017.

U.S. Provisional Patent App. No. 62/412,631 and U.S. Provisional Patent App. No. 62/543,540 are incorporated herein by reference.

FIELD OF EMBODIMENTS OF THE INVENTION

Some applications of the present invention generally relate to medical apparatus. Specifically, some applications of the present invention relate to a ventricular assist device and methods of use thereof.

BACKGROUND

Ventricular assist devices are used to assist cardiac circulation, for patients suffering from a failing heart. Most commonly a left-ventricular assist device is applied to a defective heart, in order to assist left-ventricular functioning. In some cases, a right-ventricular assist device is used, in order to assist right-ventricular functioning.

SUMMARY OF EMBODIMENTS

In accordance with some applications of the present invention, an impeller includes a helical elongate element, a spring that is disposed inside of, and coaxially with, the helical elongate element, and a film of material supported between the helical elongate element and the spring. For some applications, the impeller comprises a portion of a ventricular assist device configured to assist ventricular functioning of a subject, e.g., a left-ventricular assist device is configured to assist left ventricular functioning of a subject. The ventricular assist device typically includes an elongate tube configured to traverse the subject's aortic valve, such that a proximal end of the tube is disposed within the subject's aorta and a distal end of the tube is disposed within the subject's left ventricle. The elongate tube includes a frame formed from a self-expandable shape-memory alloy, and a blood impermeable material that is disposed upon the frame. The ventricular assist device includes a pump, which typically includes the impeller and a cage disposed around the impeller. The impeller is typically configured to pump blood out of the subject's left ventricle and into the subject's aorta, by rotating. Typically, the impeller also impedes backflow of blood across the aortic valve, from the aorta into the left ventricle.

For some applications, the cage is integrally formed with the elongate tube such that the cage is disposed within the frame of the elongate tube at the proximal end of the elongate tube. The pump is thereby disposed within a proximal portion of the elongate tube, and a longitudinal axis of the pump is thereby aligned with a longitudinal axis of the elongate tube. Alternatively, the cage is not integrally formed with the elongate tube.

There is therefore provided, in accordance with some applications of the present invention, apparatus including:

an impeller including:
- at least one helical elongate element;
- a spring, the spring being disposed inside of, and coaxially with, the helical elongate element; and
- a film of material supported between the helical elongate element and the spring.

In some applications, the impeller includes a plurality of helical elongate elements, and the film of material is supported between the plurality of helical elongate elements and the spring, such that the impeller defines a plurality of blades.

In some applications, when the impeller is disposed in a non-radially-constrained configuration, a pitch of the helical elongate element varies along a length of the helical elongate element.

In some applications, when the impeller is disposed in a non-radially-constrained configuration, a pitch of the helical elongate element is greater than 1 mm.

In some applications, when the impeller is disposed in a non-radially-constrained configuration, a pitch of the helical elongate element is less than 20 mm.

In some applications, the impeller is configured to be placed inside a blood vessel of a subject and to pump blood through the subject's blood vessel by the impeller rotating.

In some applications, the impeller is configured to be placed in an aorta of a subject and to pump blood from a left ventricle of the subject, by the impeller rotating.

In some applications, the impeller is configured to be placed in a ventricle of a subject and to pump blood from the ventricle, by the impeller rotating.

In some applications, the impeller is configured to be placed in an aorta of a subject and to impede backflow of blood from the aorta into a left ventricle of the subject.

In some applications, the impeller is configured to be radially constrained by the helical elongate element and the spring being axially elongated, and in response to the axial elongation of the helical elongate element and the spring, the film is configured to change shape without the film of material breaking.

In some applications, the apparatus further includes:

an elongate tube configured to traverse an aortic valve of a subject, such that a proximal end of the tube is disposed within an aorta of the subject and a distal end of the tube is disposed within a left ventricle of the subject, the elongate tube including:
- a frame formed from a shape-memory alloy; and
- a blood impermeable material that is disposed upon the frame; and a cage disposed around the impeller, the elongate tube being configured to be disposed around the cage and the impeller, and the impeller being configured to pump blood from the left ventricle to the aorta, by rotating.

In some applications, the spring, when disposed in a non-radially-constrained configuration thereof, is configured by virtue of its rigidity, to stabilize the impeller with respect to the elongate tube, during rotation of the impeller, such that a gap between an outer edge of the impeller and an inner surface of the elongate tube is maintained.

In some applications:

the spring defines a lumen therethrough, and the impeller further includes:

proximal and distal bushings; and a rigid shaft configured to extend from the proximal bushing to the distal bushing via the lumen defined by the spring, the rigid shaft being configured to stabilize the impeller with respect to the elongate tube, during rotation of the impeller, such that a gap between an outer edge of the impeller and an inner surface of the elongate tube is maintained.

In some applications, the cage is integrally formed with the frame of the elongate tube such that the cage is disposed within the frame of the elongate tube at the proximal end of the elongate tube, the impeller thereby being disposed within a proximal portion of the elongate tube, and a longitudinal axis of the impeller thereby being aligned with a longitudinal axis of the elongate tube.

In some applications, a gap between an outer edge of the impeller and an inner surface of the elongate tube is less than 1 mm.

In some applications, the gap between the outer edge of the impeller and the inner surface of the elongate tube is less than 0.4 mm.

In some applications, the impeller is configured to be stabilized with respect to the elongate tube, such that, during rotation of the impeller, the gap between the impeller and the elongate tube is maintained.

In some applications, the cage is not integrally formed with the frame of the elongate tube.

In some applications, the apparatus further includes one or more support arms that are configured to extend from the cage to the frame of the elongate tube, and that are configured, during rotation of the impeller, to stabilize a distal end of the impeller with respect to the frame of the elongate tube, such that a gap between an outer edge of the impeller and an inner surface of the elongate tube is maintained.

In some applications, the support arms are configured to be slidable with respect to the frame of the elongate tube.

In some applications, the support arms are configured to be coupled to the frame of the elongate tube.

In some applications, the apparatus further includes a plurality of winged projections that are coupled to the elongate tube such that planes defined by the winged projections are parallel with a longitudinal axis of the elongate tube, the winged projections being configured to stabilize turbulent blood flow that is generated by rotation of the impeller, by directing blood flow along a direction of the longitudinal axis of the elongate tube.

In some applications, the elongate tube is configured to be inserted into a body of the subject transcatheterally, while in a radially-constrained configuration, and the winged projections are configured to become folded, when the elongate tube is in its radially-constrained configuration.

In some applications, the spring defines a lumen therethrough, and the impeller further includes:

proximal and distal bushings; and a rigid shaft configured to extend from the proximal bushing to the distal bushing via the lumen defined by the spring.

In some applications, the rigid shaft is configured to maintain the proximal bushing and the distal bushing aligned with each other.

In some applications, the impeller is configured to be placed into a body of a subject, and subsequent to placement of the spring inside the subject's body, the rigid shaft is configured to be placed within the lumen defined by the spring.

In some applications, the impeller is configured to be placed into a body of a subject, and the rigid shaft is configured to be disposed within the lumen defined by the spring, during placement of the impeller into the subject's body, In some applications, the impeller further includes proximal and distal bushings, and the spring, when disposed in a non-radially-constrained configuration thereof, is configured, by virtue of its rigidity, to maintain the proximal bushing and the distal bushing aligned with each other.

In some applications, the spring, when disposed in the non-radially-constrained configuration thereof, is configured such that there are substantially no gaps between windings of the spring and adjacent windings thereto.

There is further provided, in accordance with some applications of the present invention, a method including:

placing within a blood vessel of a subject an impeller, the impeller including:

at least one helical elongate element;

a spring, the spring being disposed inside of, and coaxially with, the helical elongate element; and a film of material supported between the helical elongate element and the spring; pumping blood through the subject's blood vessel, using the impeller.

The present invention will be more fully understood from the following detailed description of embodiments thereof, taken together with the drawings, in which:

DETAILED DESCRIPTION OF EMBODIMENTS

Figure 1B:
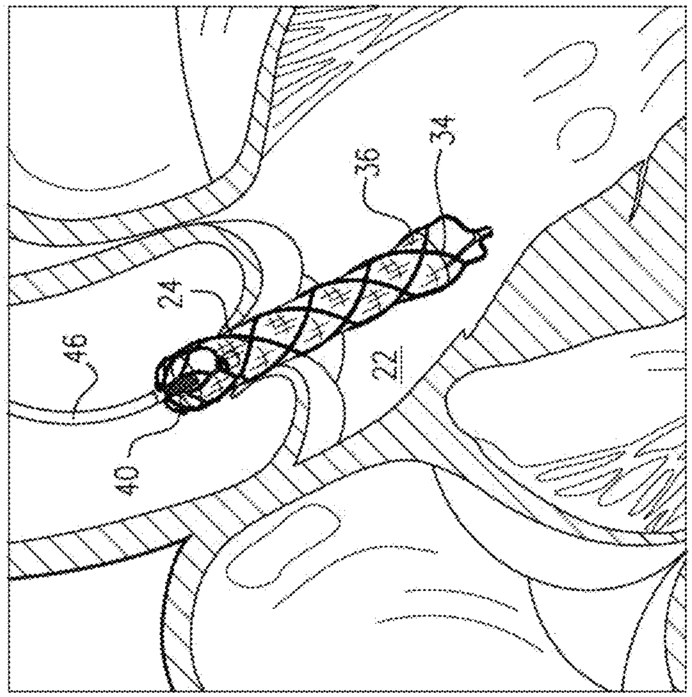
FIGS. 1A and 1B are schematic illustrations of a ventricular assist device disposed in a subject's left ventricle, in accordance with some applications of the present invention.
Figure 1A:
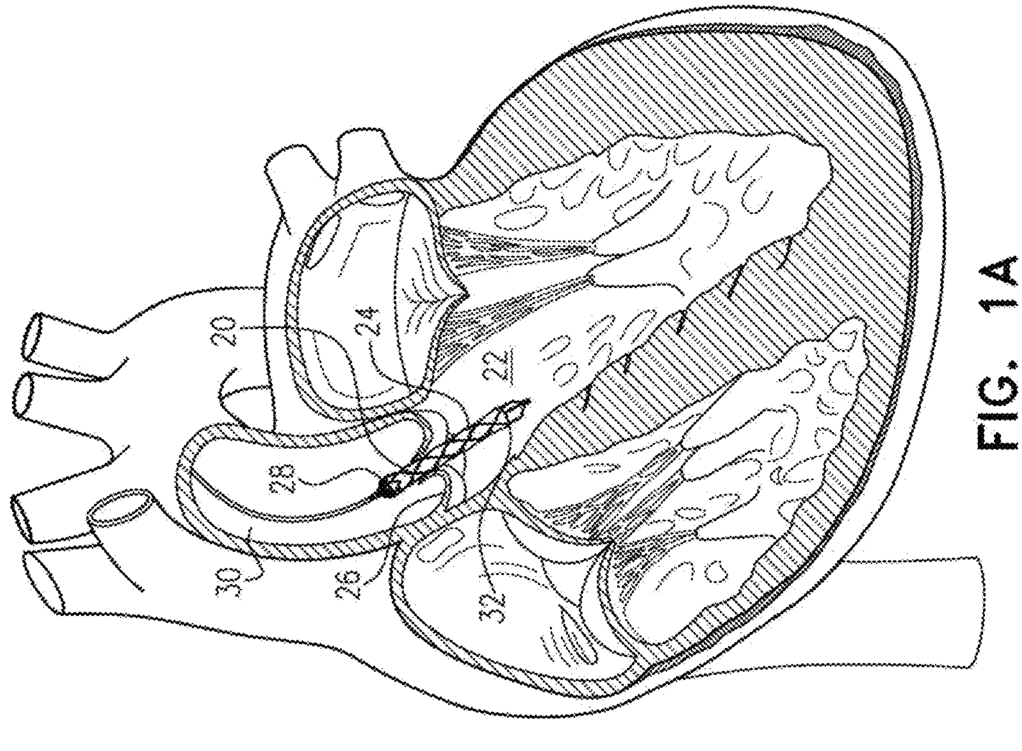

Reference is now made to FIGS. 1A and 1B, which are schematic illustrations of a ventricular assist device 20 disposed in a subject's left ventricle 22, in accordance with some applications of the present invention. The ventricular assist device includes an elongate tube 24, which traverses an aortic valve 26 of the subject, such that a proximal end 28 of the elongate tube is disposed in an aorta 30 of the subject and a distal end 32 of the tube is disposed within left ventricle 22. The elongate tube typically includes a radially-expandable frame 34 formed from a self-expandable shape-memory alloy, such as nitinol, and a blood impermeable material 36 that is disposed upon the frame. For example, the blood impermeable material may include polyurethane, polyester, and/or silicone. Typically, the frame provides the elongate tube with rigidity, and the blood impermeable material provides the elongate tube with blood impermeability. Further typically, the shape memory alloy of the frame is shape set such the frame assumes its tubular shape in the absence of any forces being applied to the tube. Typically, device 20 is inserted into the left ventricle transcatheterally (e.g., via the brachial artery), while the tube is in a radially constrained state. Upon being released from the catheter, the tube automatically assumes it tubular shape, due to the frame expanding. A pump 40 is disposed within the elongate tube (e.g., within a proximal portion of the elongate tube, as shown), and is configured to pump blood through the elongate tube from the left ventricle into the aorta, to thereby assist left ventricular functioning.

Figure 2:
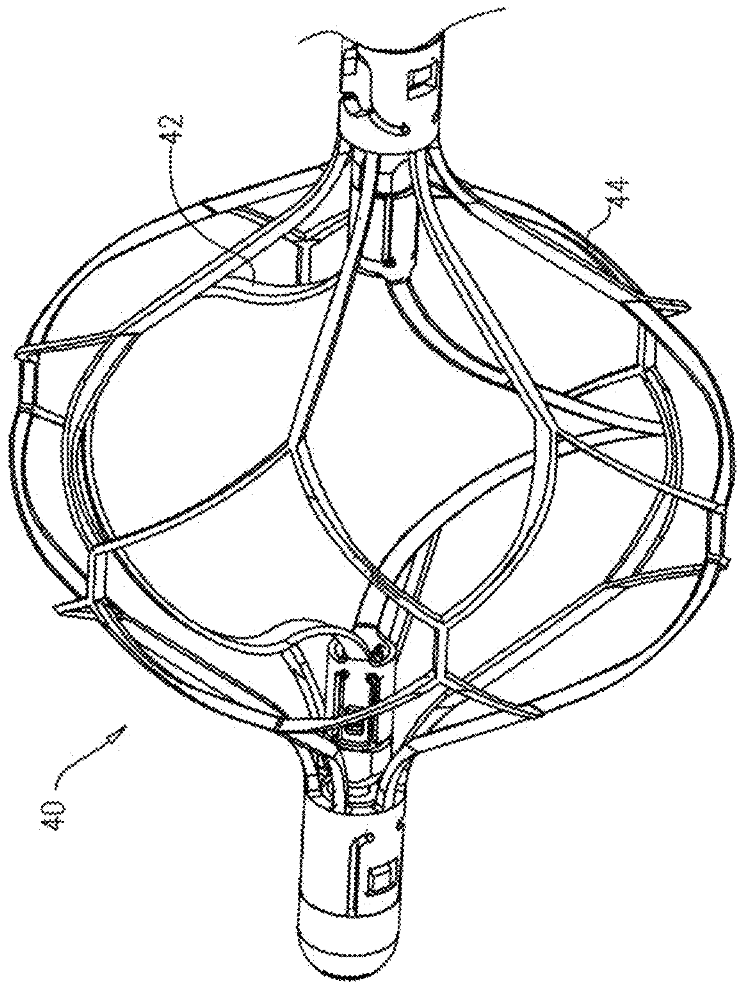
FIG. 2 is a schematic illustration of a pump that includes an impeller and a cage, in accordance with some applications of the present invention.

FIG. 2 is a schematic illustration of pump 40, in accordance with some applications of the present invention. Pump 40 typically includes a radially-expandable impeller 42 disposed inside a radially-expandable cage 44. Typically, pump 40 is inserted into the left ventricle transcatheterally, while the impeller and the cage are in radially constrained configurations. The impeller and the cage typically include a shape memory alloy (such as nitinol), which is shape set such that the impeller and the cage assume non-radially-constrained (i.e., radially-expanded) configurations thereof in the absence of any radially-constraining force acting upon the impeller and the cage. Thus, typically, the cage and the impeller radially expand upon being released from the distal end of the catheter via which they are inserted. For some applications, an engagement mechanism engages the impeller and the cage with respect to one another, such that in response to the cage becoming radially constrained the impeller becomes radially constrained, e.g., in accordance with apparatus and methods described in described in WO 14/141284 to Schwammenthal, which is incorporated herein by reference. In general, pump 40 is generally similar to the blood pumps described in WO 14/141284 to Schwammenthal, WO 15/177793 to Schwammenthal, and/or WO 16/185473 to Schwammenthal, all of which are incorporated herein by reference. Typically, pump 40 pumps blood through the elongate tube from the left ventricle into the aorta, by the impeller rotating. For some applications, a rotating cable 46 (FIG. 1B) rotates the impeller. Typically, the rotating cable is rotated by a motor (not shown) which is disposed outside the subject's body, or inside the subject's body.

For some applications, pump 40 is disposed at a proximal end of the elongate tube, such that the pump is disposed within the aorta. For some applications, the pump is disposed at the distal end of the elongate tube, such that the pump is disposed within the subject's ventricle.

Figure 3:
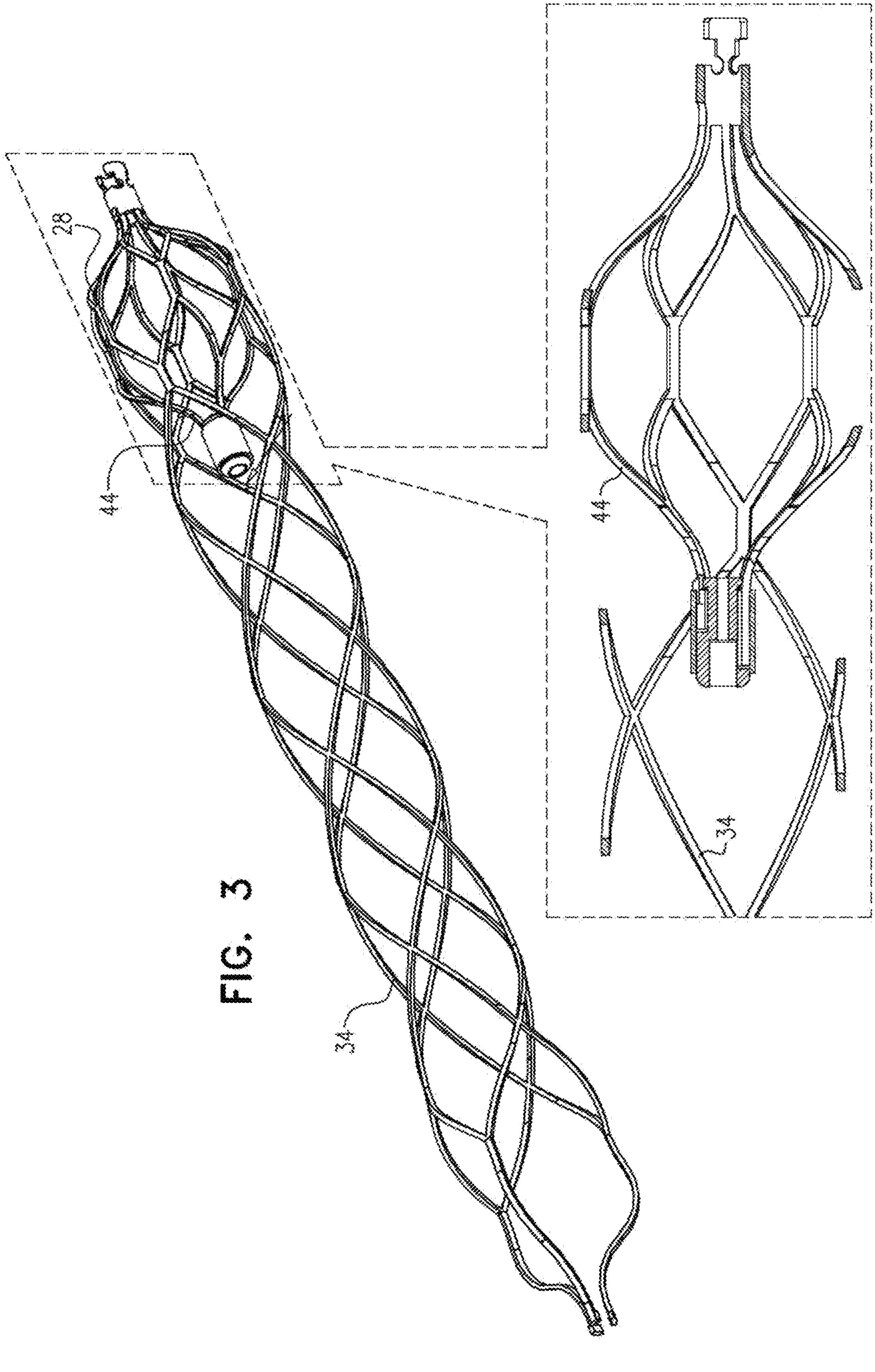
FIG. 3 is a schematic illustration of a frame of an elongate tube of the ventricular assist device, and a cage of the impeller of the ventricular assist device, in accordance with some applications of the present invention.

Reference is now made to FIG. 3, which is a schematic illustration of frame 34 of elongate tube 24 and cage 44 of pump 40 of ventricular assist device 20, in accordance with some applications of the present invention. As shown, for some applications, the cage is integrally formed with the frame of the elongate tube, such that the cage is disposed within the frame of the elongate tube at the proximal end of the elongate tube. Typically, by virtue of the cage being disposed within the frame of the elongate tube at the proximal end of the elongate tube, pump 40 is disposed within a proximal portion of the elongate tube, and the longitudinal axis of the pump is aligned with the longitudinal axis of the elongate tube. For some applications, frame 34 of elongate tube 24 and cage 44 are cut from a single piece (e.g., a single tube) of a shape memory material (e.g., a shape-memory alloy, such as nitinol). Typically, by virtue of being cut from the single piece of the shape-memory the region of the tube in which the cage is disposed is able to be radially compressed to a smaller diameter than would be possible if the cage were cut from a separate piece of the shape memory material and inserted inside the elongate tube or vice versa, ceteris paribus.

Figure 4A:
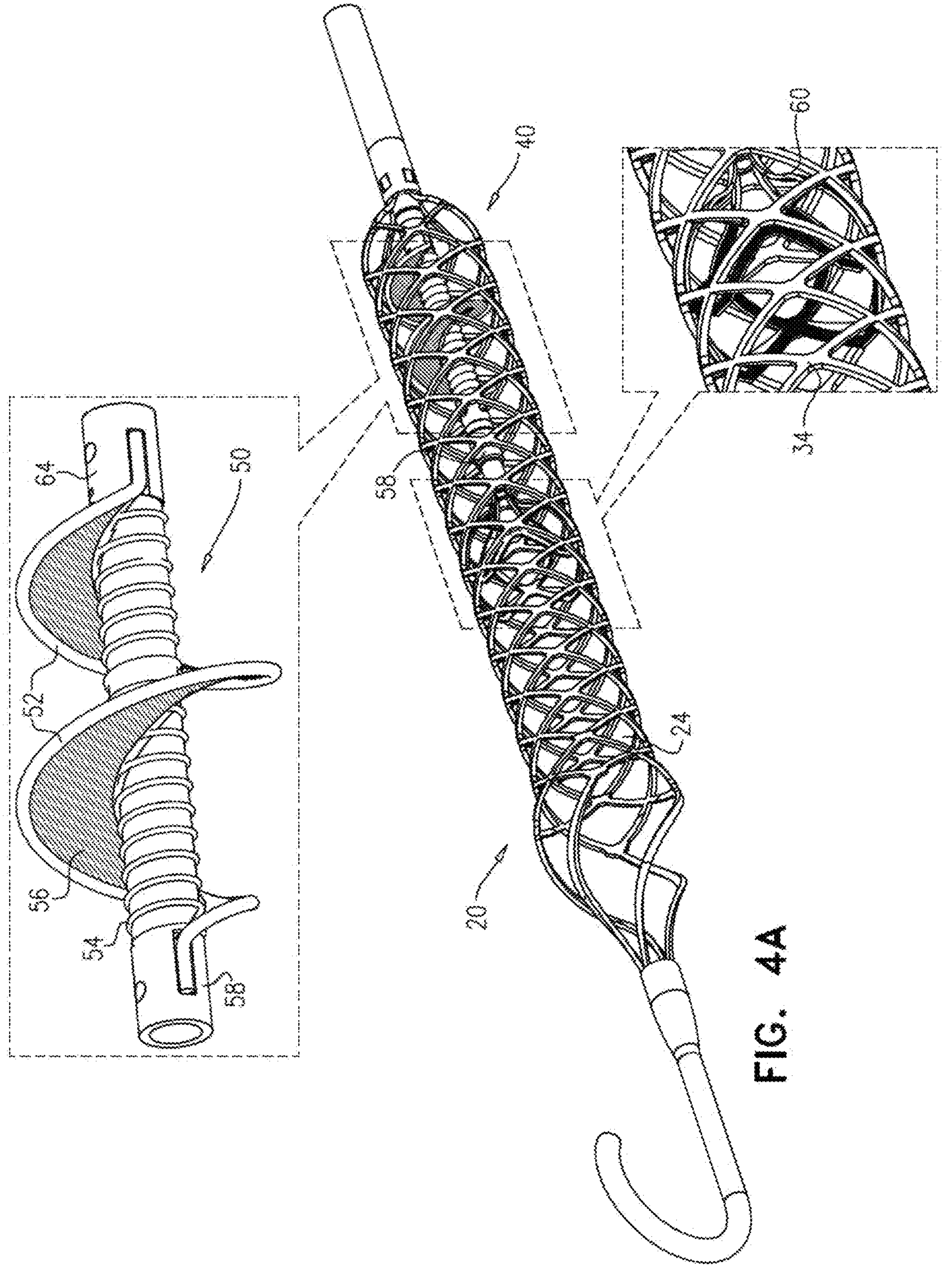
FIGS. 4A and 4B are schematic illustrations of a ventricular assist device, in accordance with some additional applications of the present invention.

Reference is now made to FIG. 4A, which is a schematic illustration of a ventricular assist device 20, in accordance with some additional applications of the present invention. For some applications, pump 40 is generally as shown in FIG. 4A. Typically, the pump includes an impeller 50, which includes an outer helical elongate element 52, which winds around a central axial spring 54, such that the helix defined by the helical elongate element is coaxial with the central axial spring. For some applications, the helical elongate element and the central axial spring are made of a shape memory material, e.g., a shape memory alloy such as nitinol. Typically, the helical elongate element and the central axial spring support a film 56 of a material (e.g., a polymer, such as polyurethane, and/or silicone) therebetween. The helical elongate element, the axial spring and the film define the impeller blade, with the helical elongate element defining the outer edge of the impeller blade (and thereby defining the outer edge of the impeller), and the axial spring defining the axis of the impeller blade. For some applications, sutures (e.g., polyester sutures, not shown) are wound around the helical elongate element, e.g., as described in WO 14/141284, which is incorporated herein by reference. Typically, the sutures are configured to facilitate bonding between the film of material (which is typically a polymer, such as polyurethane, or silicone) and the helical elongate element (which is typically a shape memory alloy, such as nitinol). For some applications, sutures (e.g., polyester sutures, not shown) are wound around spring 54. Typically, the sutures are configured to facilitate bonding between the film of material (which is typically a polymer, such as polyurethane, or silicone) and the spring (which is typically a shape memory alloy, such as nitinol).

Typically, proximal ends of both spring 54 and helical elongate element 52 are coupled to a proximal bushing (i.e., sleeve bearing) 64 of the impeller, such that the proximal ends of both spring 54 and helical elongate element 52 are disposed at a similar radial distance from the longitudinal axis of the impeller, as each other. Similarly, typically, distal ends of both spring 54 and helical elongate element 52 are coupled to a distal bushing 58 of the impeller, such that the distal ends of both spring 54 and helical elongate element 52 are disposed at a similar radial distance from the longitudinal axis of the impeller, as each other.

For some such applications, frame 34 of elongate tube 24 does not include a cage integrally formed therewith, as described hereinabove with reference to FIG. 3. Rather, for some such applications, a distal bushing 58 of the impeller is stabilized with respect to the elongate tube, by means of one or more support arms 60 that extend radially outwardly from the distal bushing of the impeller to frame 34 of elongate tube 24. As shown in FIG. 4A, for some applications, the support arms are not coupled to frame 34 of the elongate tube, but are configured to engage an inner surface of the elongate tube, to thereby stabilize the distal bushing of the impeller with respect to the elongate tube. For such applications, the support arms are typically configured to be moveable with respect to the elongate tube, by the support arms sliding along the inner surface of the elongate tube. Alternatively, even if the support arms are not integrally formed with frame 34 of the elongate tube, the support arms are coupled to frame 34 of the elongate tube (e.g., via welding, suturing, and/or an adhesive), such that, at least at the locations at which the support arms are coupled to the frame of the elongate tube, the support arms cannot undergo motion relative to the elongate tube. Further alternatively, the device includes support arms that are integrally formed with frame 34 of the elongate tube, as shown in FIG. 4B.

Figure 4B:
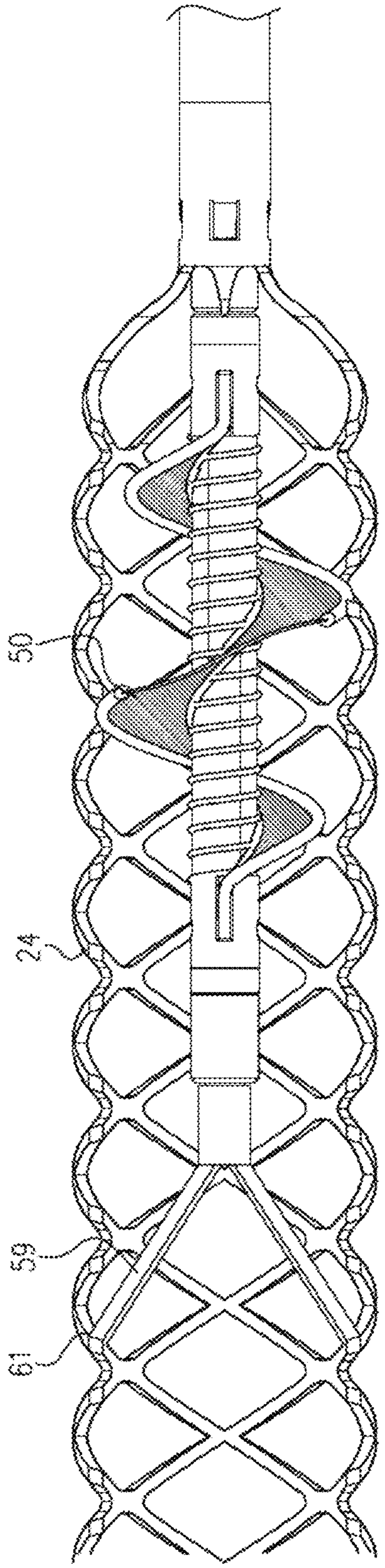

Reference is now made to FIG. 4B, which is a schematic illustration of device 20, the device including support arms 59, which are integrally formed with frame 34 of the elongate tube 24, the support arms being coupled to frame 34 at coupling points 61, in accordance with some applications of the present invention. Typically, the support arms are configured to extend from the distal bushing of the impeller to the coupling points, and are configured to thereby stabilize the distal bushing of the impeller with respect to the elongate tube.

With respect to device 20 as shown in FIGS. 4A-B, it is noted that for some applications, impeller 50 is disposed at a proximal end of the elongate tube, as shown, such that, during use of device 20, the impeller is disposed within the aorta, and pumps blood from the left ventricle into the aorta by rotating within the aorta. For some applications (not shown), the impeller is disposed at the distal end of the elongate tube, such that, during use of device 20, the impeller is disposed within the ventricle, and pumps blood out of the ventricle, by rotating within the ventricle. In general, in the context of the present application, the term "blood vessel" should be interpreted as including a ventricle. Similarly, an impeller that is described as being placed within a blood vessel, should be interpreted as including an impeller that is placed within a ventricle.

Figure 5A:
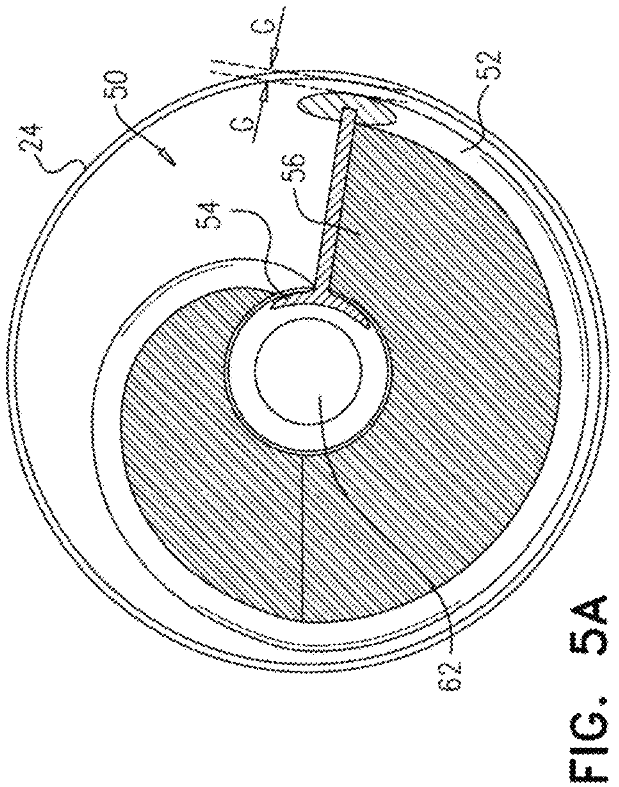
FIGS. 5A and 5B are schematic illustrations of respective cross-sectional views of an impeller of the ventricular assist device shown in FIGS. 4A and 4B in accordance with some applications of the present invention.
Figure 5B:
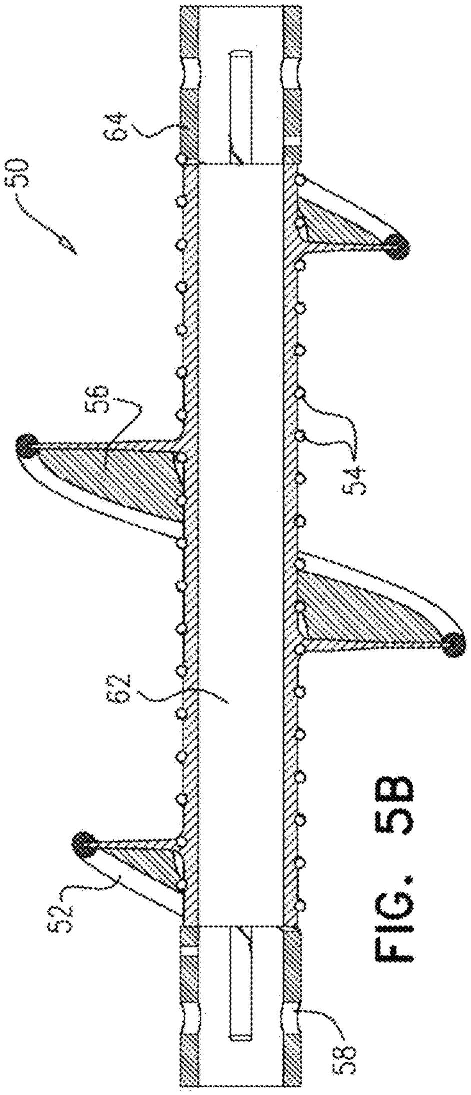
Figure 5C:
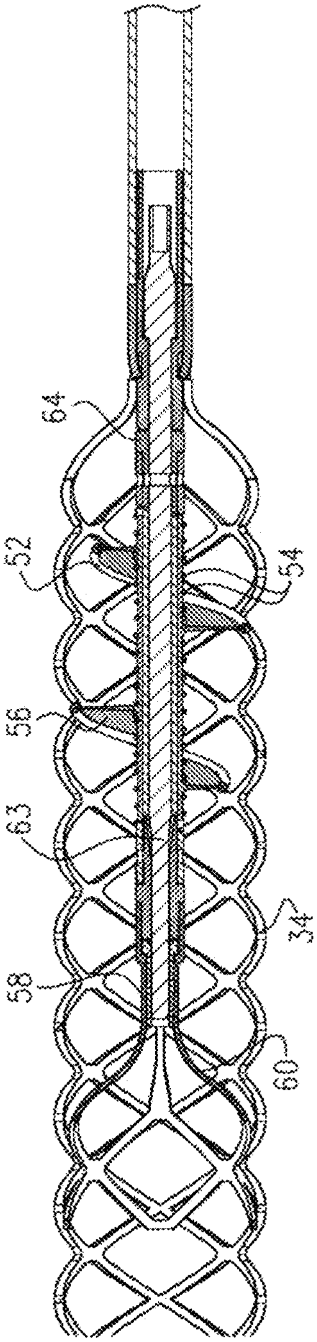
FIG. 5C is a schematic illustration of a cross-sectional view of the ventricular assist device shown in FIGS. 4A and 4B, in accordance with some applications of the present invention.

Reference is now made to FIGS. 5A and 5B, which are schematic illustrations of cross-sectional views of impeller 50, respectively perpendicularly to the longitudinal axis of the impeller, and along the longitudinal axis of the impeller, in accordance with some applications of the present invention. Reference is also made to FIG. 5C, which is a schematic illustration of a cross-sectional view of ventricular assist device 20 along the longitudinal axis of the device, in accordance with some applications of the present invention. As shown in FIG. 5B for example, spring 54 defines a lumen 62 therethrough. For some applications, a rigid shaft 63 is disposed along the lumen at least from proximal bushing 64 of the impeller to distal bushing 58. The rigid shaft is configured to impart rotational motion from the proximal bushing to the distal bushing, and/or to maintain the distal bushing and the proximal bushing aligned with each other and aligned with the longitudinal axis of the elongate tube. Alternatively or additionally, spring 54 itself acts as a shaft. Thus, for some applications, the spring imparts rotational motion from the proximal bushing to the distal bushing, and/or maintains the distal bushing and the proximal bushing aligned with each other and aligned with the longitudinal axis of the elongate tube. For some such applications, the spring is configured such that, when the spring is disposed in a non-radially-constrained configuration, there are substantially no gaps between windings of the spring and adjacent windings thereto.

Figure 5D:
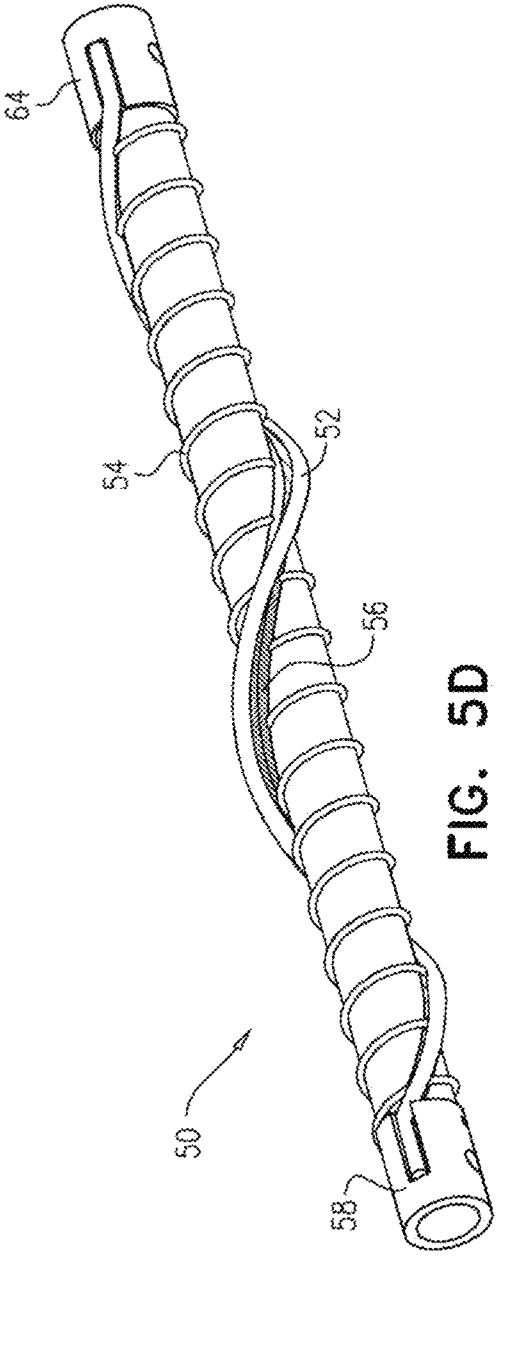
FIG. 5D is a schematic illustration of the impeller of the ventricular assist device shown in FIGS. 4A and 4B in a radially-constrained configuration, in accordance with some applications of the present invention.

Reference is now made to FIG. 5D, which is a schematic illustration of impeller 50 in a radially constrained (i.e., axially-elongated) configuration, in accordance with some applications of the present invention. Typically, pump 40 is inserted into the left ventricle transcatheterally, while impeller 50 is in its radially constrained configuration. As shown, in the radially constrained configuration, both helical elongate element 52 and central axial spring 54 become axially elongated, and radially constrained. Typically film 56 of the material (e.g., silicone) changes shape to conform to the shape changes of the helical elongate element and the axial support spring, both of which support the film of material. Typically, using a spring to support the inner edge of the film allows the film to change shape without the film becoming broken or collapsing inwardly onto a shaft disposed within lumen 62, due to the spring providing a large surface area to which the inner edge of the film bonds. For some applications, using a spring to support the inner edge of the film reduces a diameter to which the impeller can be radially constrained, relative to if, for example, a rigid shaft was to be used to support the inner edge of the film, since the diameter of the spring itself can be reduced by axially elongating the spring. As described hereinabove and as shown in FIG. 5C, for some applications, rigid shaft 63 is disposed along lumen 62 (defined by spring 54) at least from proximal bushing 64 of the impeller to distal bushing 58. For some applications, the rigid shaft is disposed inside the lumen even during the transcatheteral insertion of the impeller into the subject's left ventricle. Alternatively, the rigid shaft is advanced into lumen 62 once the impeller has already been released from the insertion catheter, and is disposed inside with subject's ventricle.

Referring again to FIG. 5A, typically there is a gap G, between the outer edge of the impeller and the inner surface of elongate tube 24, even at a location at which the span of the impeller is at its maximum. For some applications, it is desirable that the gap between the outer edge of the blade of the impeller and elongate tube 24 be relatively small, in order for the impeller to efficiently pump blood from the subject's left ventricle into the subject's aorta. However, it is also desirable that a gap between the outer edge of the blade of the impeller and elongate tube 24 be maintained, for example, in order to reduce a risk of hemolysis. For some applications, the gap G between the outer edge of the impeller and the inner surface of elongate tube 24, at the location at which the span of the impeller is at its maximum, is greater than 0.05 mm (e.g., greater than 0.1 mm), and/or less than 1 mm (e.g., less than 0.4 mm), e.g., 0.05 mm-1 mm, or 0.1 mm-0.4 mm). As described hereinabove, for some applications, distal bushing 58 of the impeller is stabilized with respect to the elongate tube, by means of one or more support arms 60, or support arms 59. For some applications, by stabilizing distal bushing 58 of the impeller with respect to the elongate tube, even a relatively small gap between the outer edge of the blade of the impeller and elongate tube 24 (e.g., a gap that is as described above) is maintained, during rotation of the impeller. Alternatively or additionally, a rigid shaft is inserted along the axis of the impeller via lumen 62 defined by spring 54, and the rigid shaft stabilizes distal bushing 58 of the impeller with respect to the elongate tube, such that even a relatively small gap between the outer edge of the blade of the impeller and elongate tube 24 (e.g., a gap that is as described above) is maintained, during rotation of the impeller. Further alternatively or additionally, spring 54 is sufficiently rigid as to stabilize distal bushing 58 of the impeller with respect to the elongate tube, such that even a relatively small gap between the outer edge of the blade of the impeller and elongate tube 24 (e.g., a gap that is as described above) is maintained, during rotation of the impeller.

Typically, the pitch of helical elongate element 52, when impeller 50 is in a non-radially-constrained configuration (e.g., inside the subject's ventricle), is greater than 1 mm (e.g., greater than 6 mm), and/or less than 20 mm (e.g., less than 10 mm). Typically, ceteris paribus, the greater the pitch of the helical elongate element (and therefore the impeller blade), the greater the blood flow that is generated by the impeller. Therefore, as described, the pitch of the helical elongate element 52, when impeller 50 is in the non-radially-constrained configuration, is typically greater than 1 mm (e.g., greater than 6 mm). On the other hand, it is typically desirable that the impeller occludes backflow from the subject's aorta into the subject's left ventricle during diastole. Ceteris paribus, it is typically the case that the smaller the pitch of the helical elongate element (and therefore the impeller blade), the greater the occlusion that is provided by the impeller. Therefore, as described, the pitch of the helical elongate element 52, when impeller 50 is in the non-radially-constrained configuration, is typically less than 20 mm (e.g., less than 10 mm).

For some applications, the pitch of the helical elongate element (and therefore the impeller blade) varies along the length of the helical elongate element, at least when the impeller is in a non-radially-constrained configuration. Typically, for such applications, the pitch increases from the distal end of the impeller (i.e., the end that is inserted further into the subject's body, and that is placed upstream with respect to the direction of antegrade blood flow) to the proximal end of the impeller (i.e., the end that is placed downstream with respect to the direction of antegrade blood flow), such that the pitch increases in the direction of the blood flow. Typically, the blood flow velocity increases along the impeller, along the direction of blood flow. Therefore, the pitch is increased along the direction of the blood flow, such as to further accelerate the blood.

For some applications (not shown), impeller 50 is generally as shown in FIGS. 4A-5D, but the impeller includes a plurality of helical elongate elements. For example, the impeller may include two or three helical elongate elements. Typically, the film of material is supported between the plurality of helical elongate elements and the spring, such that the impeller defines a plurality of blades. Typically, the number of impeller blades corresponds to the number of helical elongate elements that are disposed upon the impeller, e.g., as is generally described in WO 14/141284 to Schwammenthal, which is incorporated herein by reference.

Figure 6A:
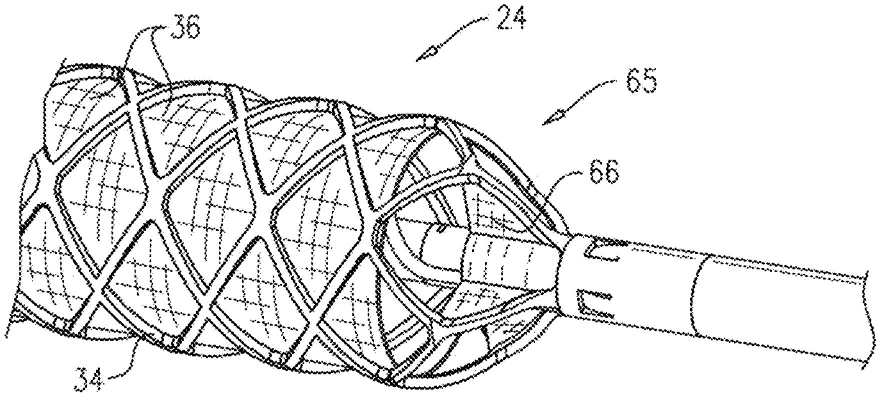
FIGS. 6A and 6B are schematic illustrations of a stator of a ventricular assist device, in accordance with some applications of the present invention.
Figure 6B:
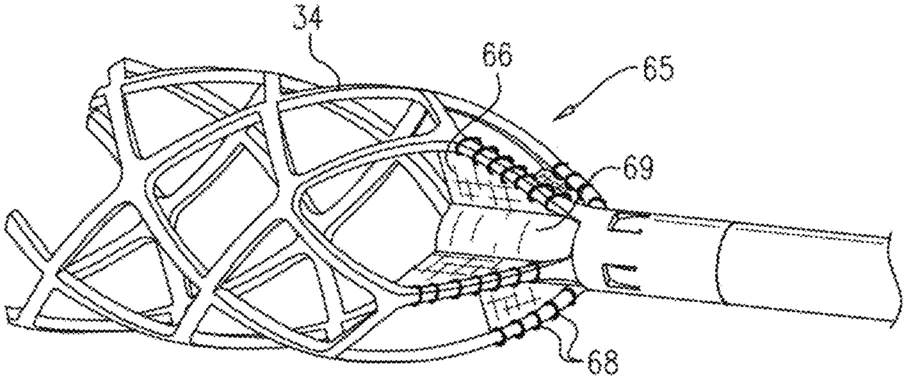

Reference is now made to FIGS. 6A and 6B, which are schematic illustrations of a stator 65 of ventricular assist device 20, in accordance with some applications of the present invention. FIG. 6B shows the stator in the absence of some other elements of the ventricular assist device, for illustrative purposes. For some applications, as shown, stator 65 is disposed within a proximal portion of frame 34 of elongate tube 24. Typically, the stator includes a plurality of (e.g., more than 2, and/or less than 8) winged projections 66 that, when device 20 is in a non-radially constrained configuration, extend from frame 34, and that are made of a flexible material, e.g., a polymer, such as polyurethane, and/or silicone. The winged projections are typically configured to define planes that are parallel to the longitudinal axis of the elongate tube, and are thereby configured to stabilize turbulent blood flow that is generated by the impeller, by directing blood flow along the direction of the longitudinal axis of the elongate tube.

It is noted that, as shown in FIG. 6A, typically elongate tube 24 includes blood impermeable material 36 that is disposed upon frame 34 of the tube. For example, the blood impermeable material may include polyurethane, polyester, or silicone, as described hereinabove. It is noted that, typically, the elongate tube includes the blood impermeable material, even though, for illustrative purposes, the blood impermeable material of the tube is not shown in all of the figures of the present application.

As shown in FIG. 6B, for some applications, sutures 68 are wound around portions of frame 34, in order to facilitate coupling between the winged projections and frame 34, in accordance with the techniques described hereinabove. For some applications, the winged projections extend from frame 34 to an axial support element 69. Typically, the axial support element is a tubular element formed of metal, plastic, and/or a polymer (such as polyurethane and/or silicone). For some applications, stator 65 is integrally formed with frame 34 of elongate tube 24. Alternatively or additionally, the stator is formed separately from the elongate tube.

As described hereinabove, typically, device 20 is inserted into the subject's ventricle transcatheterally, while elongate tube 24 is in a radially constrained state. Upon being released from the catheter, the tube automatically assumes it tubular shape, due to frame 34 of elongate tube 24 self-expanding. Typically, the stator is inserted into subject's left ventricle inside the elongate tube. During the insertion, the winged projections of the stator are in folded states, and do not substantially increase the minimal diameter to which the elongate tube can be radially-constrained, relative to if the tube did not contain the winged projections. Upon frame 34 of the elongate tube expanding, the winged projections are configured to automatically assume their winged configurations, due to the winged projections being coupled to frame 34.

It is noted that, although FIGS. 1A and 1B show ventricular assist device 20 in the subject's left ventricle, for some applications, device 20 is placed inside the subject's right ventricle, such that the device traverses the subject's pulmonary valve, and techniques described herein are applied, mutatis mutandis. Alternatively or additionally, device 20 and/or a portion thereof (e.g., impeller 50, even in the absence of elongate tube 24) is placed inside a different portion of the subject's body, in order to assist with the pumping of blood from that portion. For example, device 20 and/or a portion thereof (e.g., impeller 50, even in the absence of elongate tube 24) may be placed in a blood vessel and may be used to pump blood through the blood vessel. For some applications, device 20 and/or a portion thereof (e.g., impeller 50, even in the absence of elongate tube 24) is configured to be placed within the subclavian vein or jugular vein, at junctions of the vein with a lymph duct, and is used to increase flow of lymphatic fluid from the lymph duct into the vein, mutatis mutandis.

Figure 7A:
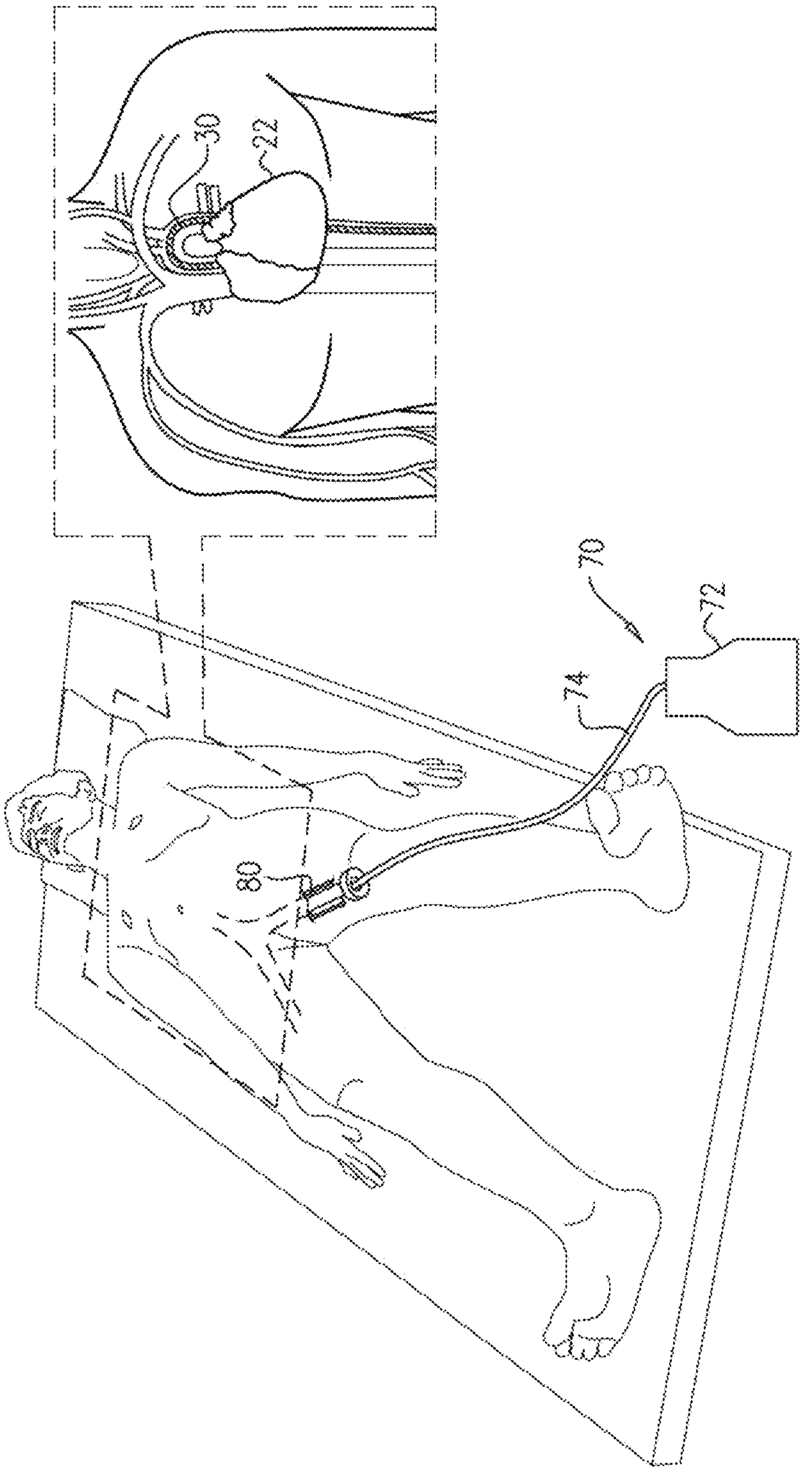
FIGS. 7A, 7B, and 7C are schematic illustrations of a ventricular assist device that includes a centrifugal pump, in accordance with some applications of the present invention.
Figure 7C:
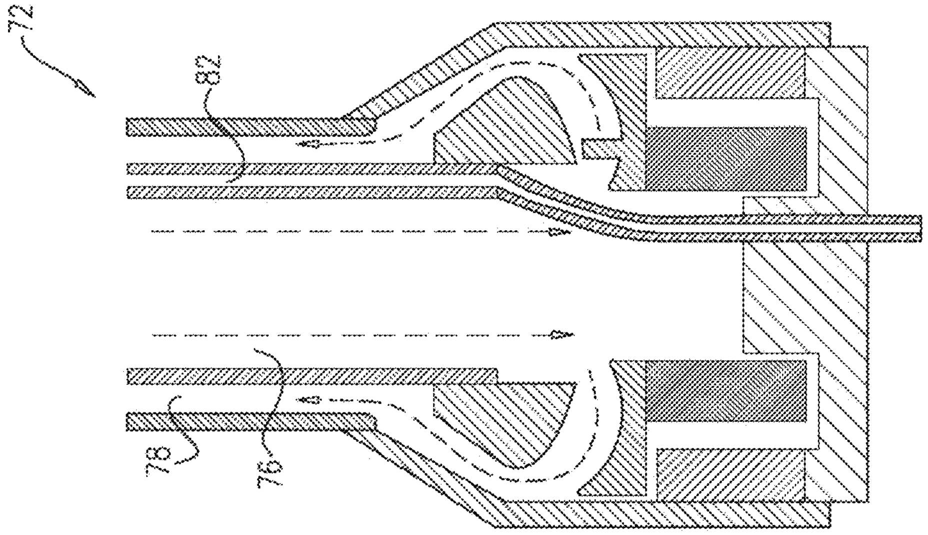
Figure 7B:
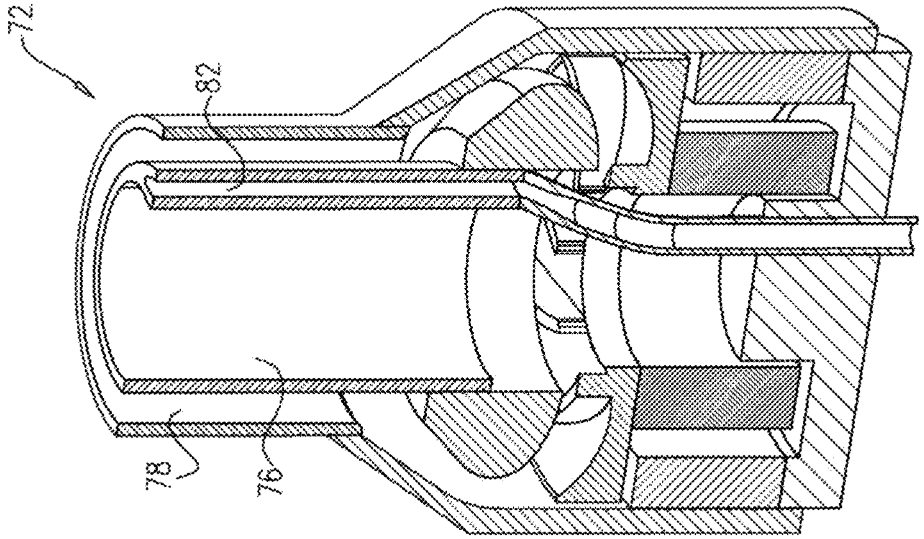

Reference is now made to FIG. 7A, which is a schematic illustration of a ventricular assist device 70 that includes a centrifugal pump 72, in accordance with some applications of the present invention. Reference is also made to FIGS. 7B and 7C, which show, respectively, three-dimensional and two-dimensional cross-sectional views of the centrifugal pump, in accordance with some applications of the present invention.

For some applications, ventricular assist device assists pumping of a ventricle (e.g., left ventricle 22) by using centrifugal pump to pump blood from the subject's left ventricle, out of the subject body, and into the subject's aorta 30. For some applications, a catheter 74 is inserted into the subject's vasculature that extends from centrifugal pump 72 to the subject's ventricle. As shown in FIGS. 7B and 7C, typically, catheter 74 defines concentric tubes 76 and 78. Blood is pumped out of the subject's left ventricle via a first one of concentric tubes (e.g., inner tube 76, as indicated by the dashed arrows indicating the direction of blood flow in FIG. 7C), and blood is pumped into the subject's aorta via a second one of the concentric tubes (e.g., outer tube 78, as shown in FIG. 7C). Typically, the first and second tubes are inserted into the subject's body via a single insertion point, e.g., femoral artery 80, as shown in FIG. 7A, or via a different insertion point, such as the subclavian artery. For some applications, centrifugal pump 72 defines an additional tube 82, via which blood pressure is measured.

The scope of the present invention includes combining any of the apparatus and methods described herein with any of the apparatus and methods described in one or more of the following applications, all of which are incorporated herein by reference:

International Patent Application PCT/IL2017/051092 to Tuval (published as WO 18/061002), filed Sep. 28, 2017, entitled "Blood vessel tube," which U.S. Provisional Patent Application 62/401,403 to Tuval, filed Sep. 29, 2016;

International Patent Application PCT/IL2016/050525 to Schwammenthal (published as WO 16/185473), filed May 18, 2016, entitled "Blood pump," which claims priority from US Provisional Patent Application 62/162,881 to Schwammenthal, filed May 18, 2015, entitled "Blood pump;"

International Patent Application PCT/IL2015/050532 to Schwammenthal (published as WO 15/177793), filed May 19, 2015, entitled "Blood pump," which claims priority from U.S. Provisional Patent Application 62/000,192 to Schwammenthal, filed May 19, 2014, entitled "Blood pump;"

International Patent Application PCT/IL2014/050289 to Schwammenthal (published as WO 14/141284), filed Mar. 13, 2014, entitled "Renal pump," which claims priority from (a) U.S. Provisional Patent Application 61/779,803 to Schwammenthal, filed Mar. 13, 2013, entitled "Renal pump," and (b) U.S. Provisional Patent Application 61/914,475 to Schwammenthal, filed Dec. 11, 2013, entitled "Renal pump;"

U.S. patent application Ser. No. 14/567,439 to Tuval (published as US 2015/0157777), filed Dec. 11, 2014, entitled "Curved catheter," which claims priority from U.S. Provisional Patent Application 61/914,470 to Tuval, filed Dec. 11, 2013, entitled "Curved catheter;" and International Patent Application PCT/IL2013/050495 to Tuval (published as WO 13/183060), filed Jun. 6, 2013, entitled "Prosthetic renal valve," which claims priority from U.S. Provisional Patent Application 61/656,244 to Tuval, filed Jun. 6, 2012, entitled "Prosthetic renal valve."

There is therefore provided, in accordance with some applications of the present invention, the following inventive concepts:

Inventive concept 1. Apparatus comprising:
- a left ventricular assist device configured to assist left ventricular functioning of a subject, the left ventricular assist device comprising:
  - an elongate tube configured to traverse an aortic valve of the subject, such that a proximal end of the tube is disposed within an aorta of the subject and a distal end of the tube is disposed within a left ventricle of the subject, the elongate tube comprising:
    - a frame formed from a shape-memory alloy; and
    - a blood impermeable material that is disposed upon the frame;
  - a rotatable impeller configured to pump blood from the subject's left ventricle to the subject's aorta by rotating; and
  - a plurality of winged projections that are coupled to the elongate tube such that planes defined by the winged projections are parallel with a longitudinal axis of the elongate tube, the winged projections being configured to stabilize turbulent blood flow that is generated by rotation of the impeller, by directing blood flow along a direction of the longitudinal axis of the elongate tube.

Inventive concept 2. The apparatus according to inventive concept 1, wherein the elongate tube is configured to be inserted into a body of the subject transcatheterally, while in a radially-constrained configuration, and wherein the winged projections are configured to become folded, when the elongate tube is in its radially-constrained configuration.

Inventive concept 3. A method comprising:
- placing an elongate tube into a body of a subject, such that the elongate tube traverses an aortic valve of the subject, such that a proximal end of the tube is disposed within an aorta of the subject and a distal end of the tube is disposed within a left ventricle of the subject, the elongate tube including:
  - a frame formed from a shape-memory alloy, and
  - a blood impermeable material that is disposed upon the frame; and
- pumping blood from the subject's left ventricle to the subject's aorta by rotating an impeller that is disposed within the elongate tube,
- a plurality of winged projections being coupled to the elongate tube such that planes defined by the winged projections are parallel with a longitudinal axis of the elongate tube, the winged projections being configured to stabilize turbulent blood flow that is generated by rotation of the impeller, by directing blood flow along a direction of the longitudinal axis of the elongate tube.

Inventive concept 4. The method according to claim inventive concept 3, wherein placing the elongate tube into the subject's body comprises placing the elongate tube into the subject's body transcatheterally while the elongate tube is in a radially-constrained configuration, the winged projections being configured to become folded, when the elongate tube is in its radially-constrained configuration.

Inventive concept 5. Apparatus comprising:
- a left ventricular assist device configured to assist left ventricular functioning of a subject, the left ventricular assist device comprising:

an elongate tube configured to traverse an aortic valve of the subject, such that a proximal end of the tube is disposed within an aorta of the subject and a distal end of the tube is disposed within a left ventricle of the subject, the elongate tube comprising:

a frame formed from a shape-memory alloy; and a blood impermeable material that is disposed upon the frame; and a pump comprising a rotatable impeller and a cage disposed around the rotatable impeller, the cage being integrally formed with the elongate tube such that the cage is disposed within the frame of the elongate tube at the proximal end of the elongate tube, the pump thereby being disposed within a proximal portion of the elongate tube, and a longitudinal axis of the pump thereby being aligned with a longitudinal axis of the elongate tube.

Inventive concept 6. A method comprising:

placing, into a subject's body, a left ventricular assist device configured to assist left ventricular functioning of a subject, the left ventricular assist device including:

an elongate tube configured to traverse an aortic valve of the subject, such that a proximal end of the tube is disposed within an aorta of the subject and a distal end of the tube is disposed within a left ventricle of the subject, the elongate tube including:

a frame formed from a shape-memory alloy, and a blood impermeable material that is disposed upon the frame, and a pump comprising a rotatable impeller and a cage disposed around the rotatable impeller, the cage being integrally formed with the elongate tube such that the cage is disposed within the frame of the elongate tube at the proximal end of the elongate tube, the pump thereby being disposed within a proximal portion of the elongate tube, and a longitudinal axis of the pump thereby being aligned with a longitudinal axis of the elongate tube; and pumping blood from the subject's left ventricle to the subject's aorta by rotating the impeller, Inventive concept 7. A blood pump for pumping blood from a first location in a body of a subject to a second location in the subject's body, the blood pump comprising:

a first tube for pumping the blood away from the first location;

a second tube for pumping the blood toward to second location, the first and second tubes being coaxial with respect to each other; and a centrifugal pump configured to pump the blood through the first and second tubes.

Inventive concept 8. A method comprising:

pumping blood from a first location in a body of a subject to a second location in the subject's body, by:

pumping the blood away from the first location via a first tube;

pumping the blood toward to second location via a second tube, the first and second tubes being coaxial with respect to each other; and using a centrifugal pump to pump the blood through the first and second tubes.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:

a tube configured to traverse an aortic valve of a subject, such that a proximal end of the tube is disposed within an aorta of the subject and a distal end of the tube is disposed within a left ventricle of the subject, the tube comprising a blood-impermeable material;

an impeller disposed inside the tube;

a frame disposed around the impeller within at least a portion of the tube;

the impeller configured to rotate such as to pump blood from the left ventricle to the aorta, the impeller being disposed inside the tube such that, when the impeller and the tube are deployed inside the subject and prior to rotation of the impeller, a radial gap between an outer edge of the impeller and an inner surface of the tube is less than 1 mm; and the impeller being radially stabilized, such that, during rotation of the impeller, a radial gap between the outer edge of the impeller and the inner surface of the tube is maintained.

2. The apparatus according to claim 1, wherein the impeller is configured to be placed within the subject's left ventricle.

3. The apparatus according to claim 1, wherein the impeller comprises at least one impeller blade defined by:

a helical elongate element; and a film of material supported at least partially by the helical elongate element.

4. The apparatus according to claim 3, wherein, when the impeller is disposed in a non-radially-constrained configuration, a pitch of the helical elongate element varies along a length of the helical elongate element.

5. The apparatus according to claim 3, wherein, when the impeller is disposed in a non-radially-constrained configuration, a pitch of the helical elongate element is greater than 1 mm.

6. The apparatus according to claim 3, wherein, when the impeller is disposed in a non-radially-constrained configuration, a pitch of the helical elongate element is less than 20 mm.

7. The apparatus according to claim 3, wherein, when the impeller and the tube are deployed inside the subject and prior to rotation of the impeller, the radial gap between the outer edge of the impeller and the inner surface of the tube is less than 0.4 mm.

8. The apparatus according to claim 3, wherein the impeller further comprises a spring disposed inside of the helical elongate element, wherein the film of material is supported between the helical elongate element and the spring to thereby define the impeller blade.

9. The apparatus according to claim 8, wherein the impeller comprises a plurality of helical elongate elements, and the film of material is supported between the plurality of helical elongate elements and the spring, such that the impeller defines a plurality of blades.

10. The apparatus according to claim 8, wherein the impeller is configured to be radially constrained by the helical elongate element and the spring being axially elongated, and wherein in response to the axial elongation of the helical elongate element and the spring, the film is configured to change shape without the film of material breaking.

11. The apparatus according to claim 8, wherein the spring, when disposed in a non-radially-constrained configuration thereof, is configured by virtue of its rigidity, to radially stabilize the impeller, during rotation of the impeller, such that the radial gap between the outer edge of the impeller and the inner surface of the tube is maintained.

12. The apparatus according to claim 8, wherein:

the spring defines a lumen therethrough, the impeller further comprises proximal and distal bushings; and a rigid shaft is configured to extend from the proximal bushing to the distal bushing via the lumen defined by the spring, the rigid shaft being configured to radially stabilize the impeller, during rotation of the impeller, such that the radial gap between the outer edge of the impeller and the inner surface of the tube is maintained.

13. The apparatus according to claim 8, wherein the spring, when disposed in a non-radially-constrained configuration thereof, is configured such that there are substantially no gaps between windings of the spring and adjacent windings thereto.

14. The apparatus according to claim 1, further comprising a plurality of winged projections that are coupled to the frame and that are configured to rectify blood flow that is generated by rotation of the impeller, by directing blood flow toward a direction of the longitudinal axis of the tube.

15. The apparatus according to claim 14, wherein the tube is configured to be inserted into a body of the subject transcatheterally, while in a radially-constrained configuration, and wherein the winged projections are configured to become folded, when the tube is in its radially-constrained configuration.

16. A method comprising:

placing a tube into a body of a subject, such that the tube traverses an aortic valve of the subject, such that a proximal end of the tube is disposed within an aorta of the subject and a distal end of the tube is disposed within a left ventricle of the subject, the tube including a blood impermeable material, an impeller being disposed inside the tube, a frame being disposed around the impeller within at least a portion of the tube, and the impeller being disposed inside the tube, such that when the impeller and the tube are deployed inside the subject's body and prior to rotation of the impeller, there is a radial gap of less than 1 mm between an outer edge of the impeller and an inner surface of the tube;

rotating the impeller, such as to pump blood from the subject's left ventricle to the subject's aorta, the impeller being radially stabilized, such that a radial gap is maintained between the outer edge of the impeller and the inner surface of the tube, during the rotation of the impeller.

17. The method according to claim 16, wherein the impeller is disposed inside the tube, such that when the impeller and the tube are deployed inside the subject's body and prior to rotation of the impeller, there is a radial gap of less than 0.4 mm between the outer edge of the impeller and the inner surface of the tube.

18. The method according to claim 16, wherein the impeller includes at least one impeller blade defined by:

a helical elongate element; and a film of material supported at least partially by the helical elongate element.

19. The method according to claim 18, wherein the impeller includes a spring disposed inside the helical elongate element, and the film of material is supported between the helical elongate element and the spring, such as to define a blade of the impeller.

20. The method according to claim 19, wherein rigidity of the spring is used to radially stabilize the impeller, during rotation of the impeller.

21. The method according to claim 19, wherein the impeller includes proximal and distal bushings a rigid shaft extends from the proximal bushing to the distal bushing via a lumen defined by the spring.

* * * * *